United States Patent
Sano et al.

(10) Patent No.: US 8,981,765 B2
(45) Date of Patent: Mar. 17, 2015

(54) MOTOR FUNCTION ANALYZING APPARATUS

(75) Inventors: Yuko Sano, Kokubunji (JP); Akihiko Kandori, Tokyo (JP); Tsuyoshi Miyashita, Tsurugashima (JP); Katsuya Morohoshi, Minamiashigara (JP); Kouichi Ishizuka, Odawara (JP)

(73) Assignee: Hitachi Maxell, Ltd., Osaka (JP)

( * ) Notice: Subject to any disclaimer, the term of this patent is extended or adjusted under 35 U.S.C. 154(b) by 421 days.

(21) Appl. No.: 13/094,856

(22) Filed: Apr. 27, 2011

(65) Prior Publication Data
US 2011/0267042 A1 Nov. 3, 2011

(30) Foreign Application Priority Data
Apr. 28, 2010 (JP) ................. 2010-104045

(51) Int. Cl.
| | |
|---|---|
| G01B 7/14 | (2006.01) |
| G01B 7/30 | (2006.01) |
| A61B 5/103 | (2006.01) |
| A61B 5/117 | (2006.01) |
| A61B 5/05 | (2006.01) |
| A61B 5/11 | (2006.01) |

(52) U.S. Cl.
CPC ............. *G01B 7/14* (2013.01); *A61B 5/1125* (2013.01); *A61B 2560/0223* (2013.01)
USPC ........... 324/207.11; 324/207.17; 324/207.22; 600/595; 600/587; 600/409

(58) Field of Classification Search
CPC ......... B60L 13/06; G01D 5/147; G01D 5/145
USPC .................................................. 324/207.11
See application file for complete search history.

(56) References Cited

U.S. PATENT DOCUMENTS

| | | | | |
|---|---|---|---|---|
| 6,161,032 | A * | 12/2000 | Acker | 600/424 |
| 6,516,212 | B1 * | 2/2003 | Bladen et al. | 600/424 |
| 6,933,846 | B2 * | 8/2005 | Moldavsky et al. | 340/568.1 |

(Continued)

FOREIGN PATENT DOCUMENTS

| | | |
|---|---|---|
| JP | 2005-095197 A | 4/2005 |
| JP | 2005-152053 A | 6/2005 |
| JP | 2008-246126 A | 10/2008 |

OTHER PUBLICATIONS

Keisuke Shima, Toshio Tsuji, Eriko Kan, Akihiko Kandori, Masaru Yokoe, and Saburo Sakoda, Measurement and Evaluation of Finger Tapping Movements Using Magnetic Sensors, 30th Annual International IEEE EMBS Conference Vancouver, British Columbia, Canada, Aug. 20-24, 2008, pp. 5628-5631.*

(Continued)

*Primary Examiner* — Jermele M Hollington
*Assistant Examiner* — Christopher McAndrew
(74) *Attorney, Agent, or Firm* — Mattingly & Malur, PC

(57) ABSTRACT

It is an object of the present invention to provide a motor function analyzing apparatus which simplifies a calibration measurement necessary before measuring a finger tapping motion, and which is capable of evaluating a motor function highly precisely. The present invention provides a motor function analyzing apparatus which simplifies a calibration measurement necessary before measuring a finger tapping motion, and which is capable of evaluating a motor function highly precisely by using a calibration point unique to each apparatus and a calibration point unique to each subject.

8 Claims, 26 Drawing Sheets

(56) References Cited

U.S. PATENT DOCUMENTS

| | | | |
|---|---|---|---|
| 7,402,996 B2* | 7/2008 | Arai et al. | 324/207.17 |
| 7,463,020 B2* | 12/2008 | Kuhn | 324/207.11 |
| 2005/0148844 A1* | 7/2005 | Ogata et al. | 600/407 |
| 2007/0272599 A1* | 11/2007 | Miyashita et al. | 209/527 |
| 2008/0238414 A1* | 10/2008 | Miyashita et al. | 324/207.22 |
| 2009/0069663 A1* | 3/2009 | Kandori et al. | 600/409 |
| 2009/0118648 A1* | 5/2009 | Kandori et al. | 600/595 |
| 2009/0192418 A1* | 7/2009 | Miyashita et al. | 600/595 |
| 2010/0106060 A1* | 4/2010 | Tsuji et al. | 600/587 |

OTHER PUBLICATIONS

Keisuke Shima, Eriko Kan, Toshio Tsuji, Toko Tsuji, Akihiko Kandori, Tsuyoshi Miyashita, Masaru Yokoe, and Saburo Sakoda, A New Calibration Method of Magnetic Sensors for Measurement of Human Finger Tapping Movements, (2007) Society of Instrument and Control Engineers, vol. 43, No. 9, 821/828.*

Additional English Translation of Section 2.1 of Shima.*

A. Kandori et al., Quantitative magnetic detection of finger movements in patients with Parkinson's disease, Neuroscience Research, vol. 49, No. 2, pp. 253-260, 2004.

K. Shima et al., A New Calibration Method of Magnetic Sensors for Measurement of Human Finger Tapping Movements, Society of Instrument and Control Engineers, vol. 43, No. 9, pp. 821-828, 2007.

Shima et al., A New Calibration Method of Magnetic Sensors for Measurement of Human Finger Tapping Movements, 2007 SICE. (Partial Translation).

* cited by examiner

FIG.16

2700 CONTROL SCREEN IMAGE

2702 MEASUREMENT DATA LIST PORTION

MOTOR FUNCTION MEASUREMENT-MAIN

○ SUBJECT DATA　　◉ MEASUREMENT DATA — 2708

MEASUREMENT DATA

| SUBJECT ID | FULL NAME | MEASUREMENT DATE | MEASUREMENT TIME | MEASUREMENT INTERVAL | MEASUREMENT METHOD | AGE | SEX | COMMENT 1 | COMMENT 2 |
|---|---|---|---|---|---|---|---|---|---|
| ID000001 | Tarou Hitachi | 2006/02/22 | 11:24:22 | 20 sec | Both Hands | 53 | Male | Very tired | Lack of Sleep |
| ID000001 | Tarou Hitachi | 2006/09/21 | 14:31:56 | 10 sec | Left Hand | 53 | Male | | |
| ID000001 | Tarou Hitachi | 2006/10/05 | 14:42:45 | 10 sec | Left Hand | 53 | Male | Headachy | |
| ID000001 | Tarou Hitachi | 2006/10/19 | 14:44:40 | 20 sec | Right Hand | 53 | Male | | |
| ID000001 | Tarou Hitachi | 2006/11/01 | 14:46:31 | 30 sec | Both Hands | 53 | Male | Right hand | |
| ID000001 | Tarou Hitachi | 2006/11/15 | 14:48:13 | 20 sec | Both Hands | 53 | Male | | |
| ID000001 | Tarou Hitachi | 2006/11/29 | 14:49:46 | 60 sec | Left Hand | 53 | Male | | |
| ID000001 | Tarou Hitachi | 2006/12/14 | 15:08:38 | 10 sec | Right Hand | 53 | Male | | |
| ID000001 | Tarou Hitachi | 2006/12/28 | 15:10:30 | 20 sec | Both Hands | 53 | Male | | |
| ID000001 | Tarou Hitachi | 2007/01/11 | 15:13:57 | 30 sec | Both Hands | 53 | Male | | |
| ID000001 | Tarou Hitachi | 2007/01/25 | 15:16:18 | 20 sec | Both Hands | 53 | Male | | |
| ID000001 | Tarou Hitachi | 2007/02/08 | 15:18:28 | 60 sec | Both Hands | 53 | Male | | |
| ID000001 | Tarou Hitachi | 2007/02/22 | 16:33:22 | 60 sec | Left Hand | 53 | Male | | |
| ID000002 | Hanako Hitachi | 2022/02/07 | 16:33:22 | 60 sec | Left Hand | 53 | Female | | |

OPERATIONS
- NEW MEASUREMENT — 2720 (FIRST CONTROL)
- MEASUREMENT — 2722 (FIRST CONTROL)
- DATA ANALYSIS — 2724 (SECOND CONTROL)
- INTER-ANNUAL DISPLAY — 2726 (THIRD CONTROL)
- MEASUREMENT DATA DELETION
- EXPORT — 2706 OPERATION (FUNCTION) BUTTON PORTION

TOOLS
- DATA MANAGEMENT
- OPTION
- END

SEARCH CONDITION — 2704 SEARCH CONDITION INPUTTING PORTION

SUBJECT ID　　　　MEASUREMENT DATE ▽ ~ 
FULL NAME　　　　MEASUREMENT METHOD
SEX ▽　　　　COMMENT 1
AGE ~　　　　COMMENT 2

[SEARCH START]　[CLEAR CONDITIONS]

MAIN SCREEN IMAGE (MEASUREMENT DATA LIST SCREEN IMAGE)

FIG. 17

MOTOR FUNCTION MEASUREMENT-MAIN

⊙ SUBJECT DATA  ○ MEASUREMENT DATA

2802 SUBJECT DATA LIST PORTION

SUBJECT DATA — 2708

| SUBJECT ID | FULL NAME | BIRTH DATE | SEX | DOMINANT HAND | MEMO |
|---|---|---|---|---|---|
| ID000001 | Tarou Hitachi | 1953/12/25 | Male | Left Hand | Sample data |
| ID000002 | Hanako Hitachi | 1955/11/25 | Female | Right Hand | |
| ID000003 | Jirou Hitachi | 1954/08/25 | Male | Both Hands | |
| ID000004 | Tugiko Hitachi | 1955/09/05 | Female | Right Hand | |
| ID000005 | Saburou Hitachi | 1956/09/15 | Male | Left Hand | |
| ID000006 | Miko Hitachi | 1957/08/26 | Female | Unknown | |
| ID000007 | Sirou Hitachi | 1958/10/07 | Male | Both Hands | |
| ID000008 | Yotuko Hitachi | 1959/10/18 | Female | Right Hand | |
| ID000009 | Gorou Hitachi | 1960/10/28 | Male | Left Hand | |
| ID000010 | Ituko Hitachi | 1961/11/08 | Female | Unknown | |
| ID000011 | Muturou Hitachi | 1962/11/19 | Male | Both Hands | |
| ID000012 | Mutuko Hitachi | 1963/11/30 | Female | Right Hand | |
| ID000013 | Sitirou Hitachi | 1964/12/10 | Male | Left Hand | |
| ID000014 | Nanako Hitachi | 1965/12/21 | Female | Unknown | |
| ID000015 | Hatirou Hitachi | 1967/01/01 | Male | Both Hands | |
| ID000016 | Yatuko Hitachi | 1968/01/12 | Female | Right Hand | |
| ID000017 | Kyuurou Hitachi | 1969/01/22 | Male | Left Hand | |
| ID000018 | Kyuuko Hitachi | 1970/02/02 | Female | Both Hands | |
| ID000019 | Jyuurou Hitachi | 1971/02/13 | Male | Both Hands | |

SEARCH CONDITION

SUBJECT ID: [ ]
FULL NAME: [ ]
SEX: [ ▽ ]

2804 SEARCH CONDITION INPUTTING PORTION
MAIN SCREEN IMAGE (SUBJECT DATA LIST SCREEN IMAGE)

[SEARCH START]
[CLEAR CONDITIONS]

OPERATIONS

[NEW MEASUREMENT] — 2720 (FIRST CONTROL)
[MEASUREMENT] — 2722 (FIRST CONTROL)

SUBJECT INFORMATION SETTINGS

[ADDITION]
[CHANGE]
[DELETION]

TOOLS

[DATA MANAGEMENT] — 2806 OPERATION (FUNCTION) BUTTON PORTION
[OPTION]
[END]

FIG.18

| MOTOR FUNCTION MEASUREMENT-SUBJECT INFORMATION SETTINGS ☒ |
|---|
| PLEASE SET SUBJECT INFORMATION |
| SUBJECT ID     [_____] |
| FULL NAME    [_____] |
| BIRTH DATE   [2007/03/08 ▽] |
| SEX            ⊙ Male    ○ Female |
| DOMINANT HAND ⊙ Left Hand   ○ Right Hand ○ Both Hands ○ Unknown |
| MEMO       [_____] |
| [OBTAIN INFORMATION FROM SUBJECT ID]    [SAVE]   [CLOSE] |

SUBJECT INFORMATION SETTINGS SCREEN IMAGE

MEASUREMENT SETTING SCREEN IMAGE

OPTION SCREEN IMAGE (MEASUREMENT SETTING TAB)

OPTION SCREEN IMAGE (PERFORMING OF MEASUREMENT TAB)

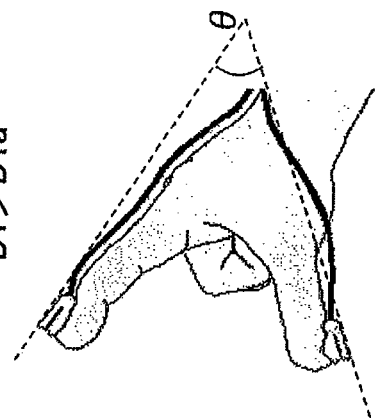
FIG.31B θ>0° D1<D1a
FIG.31C θ>0° D1>D1a
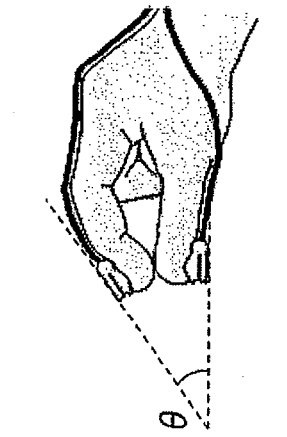
FIG.31A1 θ≒0°
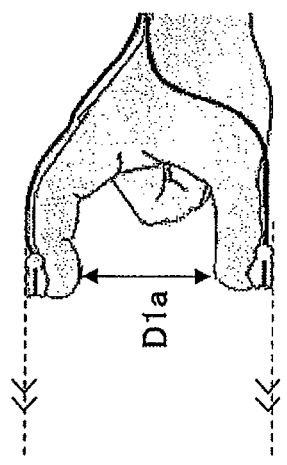
FIG.31A2
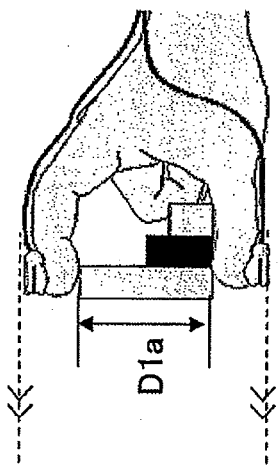

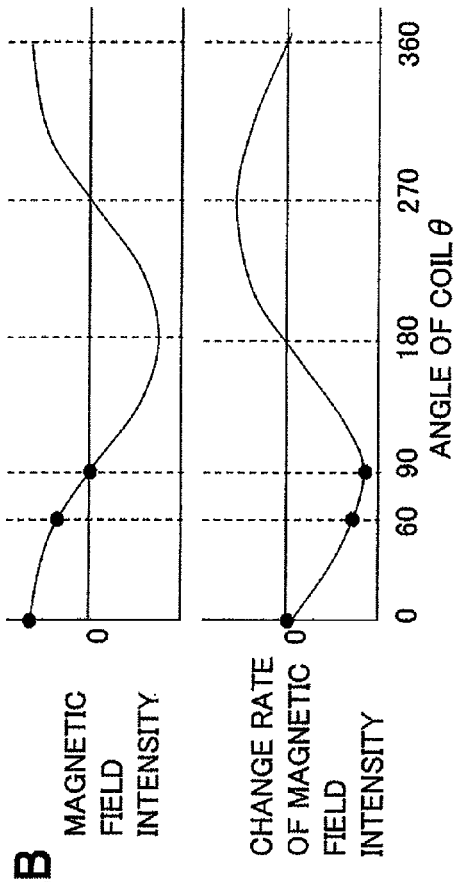
FIG.32A
FIG.32B
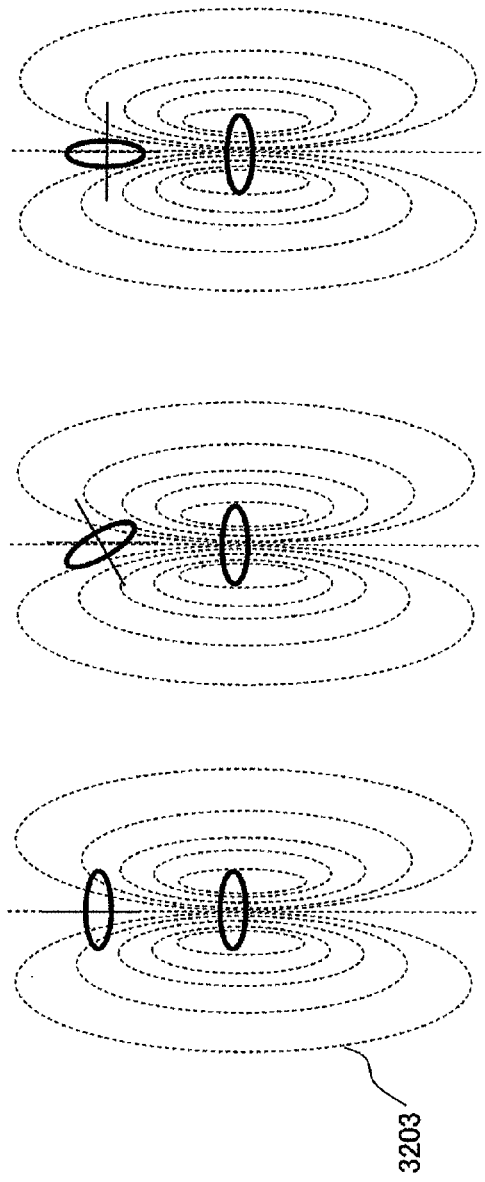
FIG.32C  θ=0°
FIG.32D  θ=60°
FIG.32E  θ=90°

MOTOR FUNCTION ANALYZING APPARATUS

CLAIM OF PRIORITY

The present application claims priority from Japanese Patent Application JP 2010-104045 filed on Apr. 28, 2010, the content of which is hereby incorporated by reference into this application.

BACKGROUND OF THE INVENTION

1. Field of the Invention

The present invention relates to a motor function analyzing apparatus that evaluates a motor function of a biological object using a magnetic sensor.

2. Description of the Related Art

Recently, the number of patients with movement disorder increases together with the progression of an aging society. Examples of such movement disorder are diseases that progress a disorder in motor function, such as Parkinson's disease, stroke, cervical myelopathy, dementia, and mental disorder. For example, Parkinson's disease that is a typical disease with movement disorder is an intractable disease which brings about a serious disorder in daily life because of tremor of hands, muscles rigidity, etc. The number of Parkinson's disease patients in Japan reaches 145,000 according to the survey by Japan Ministry of Health, Labor and Welfare in 2005, and it is expected that such number increases thereafter.

Conventionally, it is typical that a doctor checks and sees the motion of a patient and makes an evaluation based on scores representing severity levels in order to diagnose movement disorder. For example, in the case of a diagnosis to Parkinson's disease, a UPDRS (Unified Parkinson's Disease Rating Scale) is widely used as an evaluation index representing the severity level of Parkinson's disease. According to the UPDRS, a motor function is evaluated through plural motions, such as walking, and finger tapping motion (a motion of repeatedly opening/closing the thumb of a hand and the index finger thereof).

According to the UPDRS, however, evaluation is made through the subjective diagnosis by a doctor, so that there is an individual difference among doctors, resulting in insufficient objectivity in some cases. In order to overcome such a problem, apparatuses which measure the finger tapping motion by a patient using a magnetic sensor, and which evaluate a motor function quantitatively have been developed (see, for example, JP 2005-152053 A, JP 2008-246126 A and Kandori et al., "Quantitative magnetic detection of finger movements in patients with Parkinson's disease.", Neuroscience Research. Vol. 49, No. 2, 2004, pp 253-260).

According to such apparatuses, magnetic sensors are attached to respective nail portions of a thumb and an index finger (hereinafter, referred to as "two fingers"), and a voltage value obtained from the magnetic sensors is converted into a distance value between the two fingers (corresponding to a distance between respective cushion sides of the thumb and the index finger). For example, a Non-patent Literature (Keisuke SHIMA, Eriko KAN, Toshio TSUJI, Tokuo TSUJI, Akihiko KANDORI, Tsuyoshi MIYASHITA, Masaru YOKOE, and Saburo SAKODA, "Magnetic sensor calibration for human finger tap measurement", Society of Instrument and Control Engineers, Vol. 43, No. 9, 2007, pp 821-828) discloses a technology which measures three calibration points (e.g., data on three distances: 2 cm; 3 cm; and 6 cm) for the two fingers attached with magnetic sensors before measuring a finger tapping motion in order to obtain a correspondence between a voltage value and a distance value, and which substitutes such calibration points into a predetermined formula, thereby deriving a conversion formula of calculating a distance value from a voltage value.

According to the conventional technologies, however, when a calibration measurement includes an error, a calculated distance value may also include a large error in some cases. For example, when the two fingers are widely opened, even if the actual distance value between the two fingers is 15 cm, a value exceeding 30 cm may be falsely output in some cases. Also, according to the conventional technologies, it is necessary to perform three kinds of calibration measurement before a finger tapping motion is measured for every measurement, the management of instruments and the calibration measurement are bothersome.

SUMMARY OF THE INVENTION

The present invention has been made in view of the foregoing circumstances, and it is an object of the present invention to provide a motor function analyzing apparatus which simplifies a necessary calibration measurement before measuring a finger tapping motion, and which is capable of evaluating a motor function with high precision.

In order to achieve the above object, a first aspect of the present invention provides a motor function analyzing apparatus that includes: a movement-waveform generating unit which includes a magnetic field generator that generates a magnetic field, the magnetic field generator being attached to predetermined two locations of a biological object, the predetermined two locations changing a distance therebetween due to a motion of the biological object, and a magnetic field detector that detects the magnetic field, the movement-waveform generating unit generating a movement waveform based on magnetic field data detected by the magnetic field detector.

The movement-waveform generating unit includes: a calibration-point measuring unit that measures a calibration point including distance data between the predetermined two locations of the biological object and magnetic field data detected by the magnetic field detector; a conversion-formula generating unit that generates a conversion formula which converts the magnetic field data detected by the magnetic field detector into a movement waveform using the calibration point measured by the calibration-point measuring unit; and a movement-waveform generating unit that converts the magnetic field data detected by the magnetic field detector and generates a movement waveform using the conversion formula generated by the conversion-formula generating unit.

The calibration-point measuring unit includes: an apparatus-unique-voltage measuring unit that measures a voltage unique to each motor function analyzing apparatus with the magnetic field generator and the magnetic field detector being located apart from each other by a predetermined distance; and an subject-unique-voltage measuring unit that measures a voltage unique to each subject with the predetermined two locations of the biological object to which the magnetic field generator and the magnetic field detector are attached being maintaining a predetermined distance between the predetermined two locations.

The other configurations of the present invention will be explained in embodiments of the present invention to be discussed later.

BRIEF DESCRIPTION OF THE DRAWINGS

FIG. 16 is a diagram showing an illustrative screen of a measurement data list;

FIG. 17 is a diagram showing an illustrative screen of an subject data list;

FIG. 18 is a diagram showing an illustrative subject-information setting screen;

FIG. 31A1 is a diagram showing a change in the conditions of two fingers during a finger tapping motion;

FIG. 31A2 is a diagram showing a change in the conditions of two fingers during a finger tapping motion;

FIG. 31B is a diagram showing a change in the conditions of two fingers during the finger tapping motion;

FIG. 31C is a diagram showing a change in the conditions of two fingers during the finger tapping motion;

FIG. 32A is a diagram for explaining generation of a magnetic field and detection thereof;

FIG. 32B is a diagram for explaining generation of a magnetic field and detection thereof;

FIG. 32C is a diagram for explaining generation of a magnetic field and detection thereof;

FIG. 32D is a diagram for explaining generation of a magnetic field and detection thereof; and FIG. 32E is a diagram for explaining generation of a magnetic field and detection thereof.

DETAILED DESCRIPTION OF THE PREFERRED EMBODIMENTS

Embodiments for carrying out the present invention (hereinafter, simply referred to as "embodiments") will be explained in detail with reference to the accompanying drawings.

First Embodiment

Figure 1:
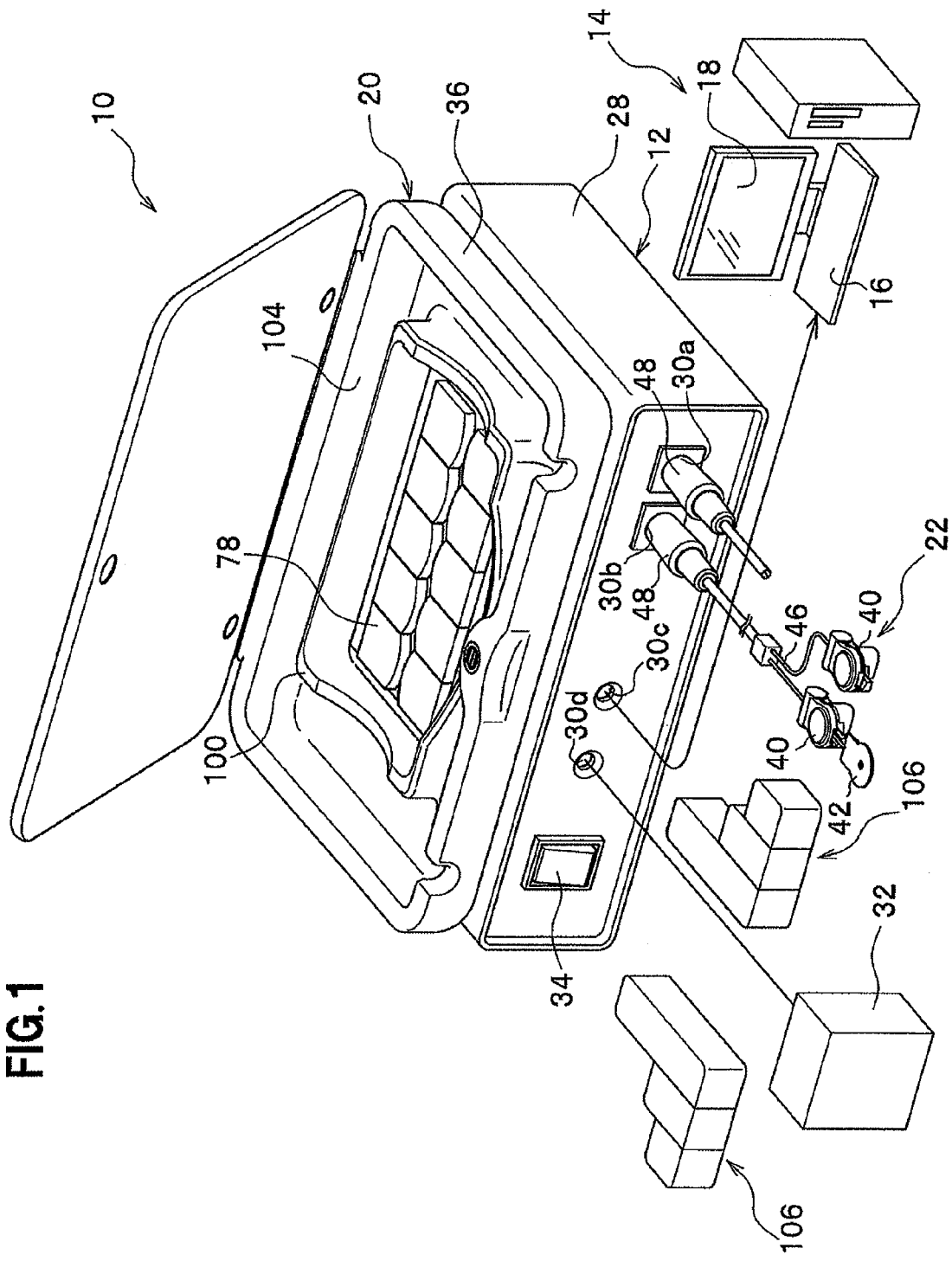
FIG. 1 is a schematic perspective view showing a motor function measuring system according to a first embodiment.
Figure 2:
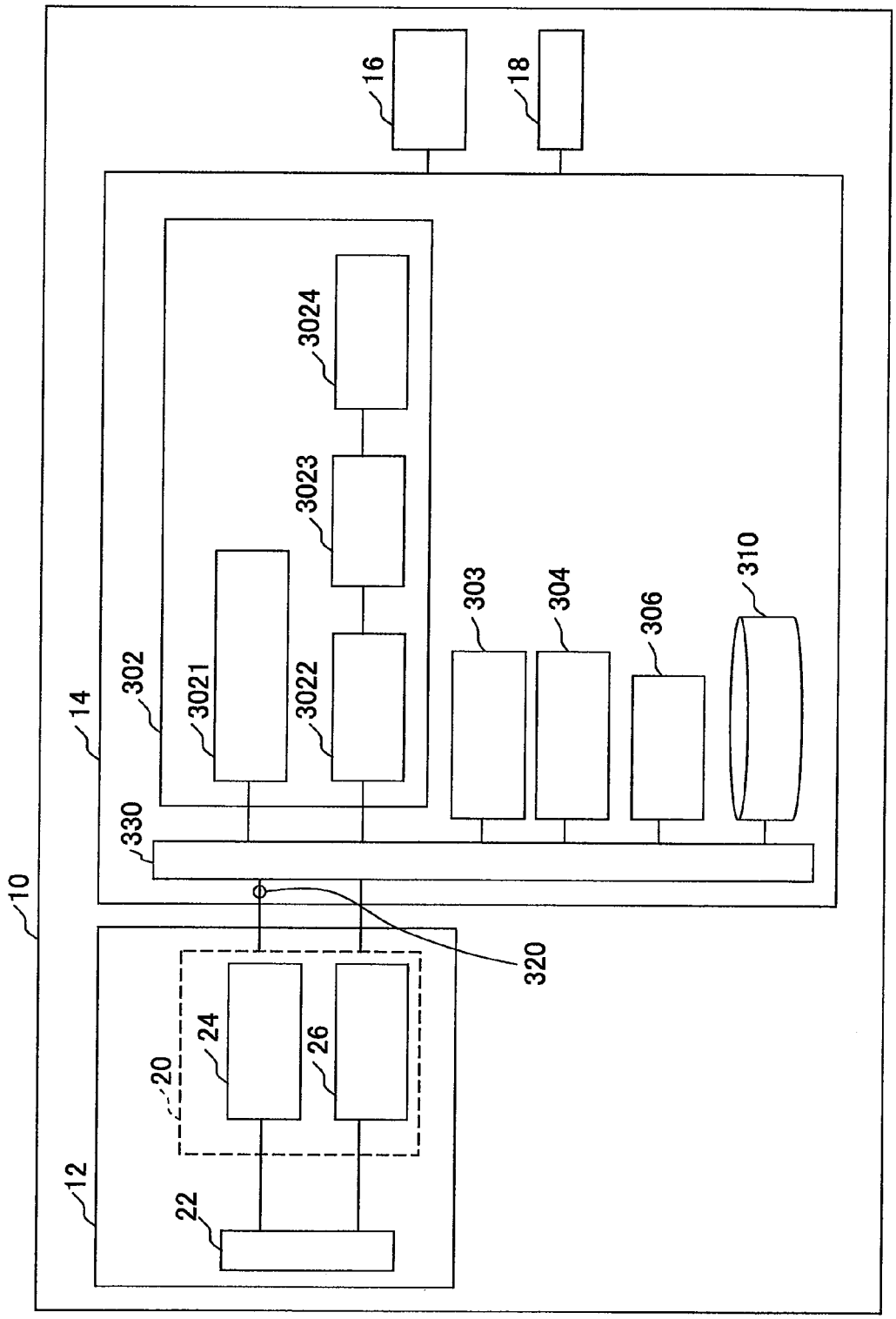
FIG. 2 is a block diagram showing an overall configuration of the motor function measuring system according to the first embodiment.

FIG. 1 is a schematic perspective view showing a motor function measuring system including a motor function analyzing apparatus according to an embodiment of the present invention. FIG. 2 is a block diagram showing an overall configuration of the motor function measuring system. The explanation will be given with reference to those drawings.

As shown in FIG. 1, a motor function measuring system 10 includes a motor function measuring apparatus 12 that measures motions of fingers of an subject (a test subject), a motor function analyzing apparatus 14 that records and analyzes data measured by the motor function measuring apparatus 12, an operation input unit 16 for inputting information on the subject, a display unit 18 that displays a measurement result and an analysis result received from the motor function analyzing apparatus 14, and an housing member 20 that houses various measuring instruments thereinside. In FIG. 1, the motor function measuring apparatus 12 is enlarged compared to the motor function analyzing apparatus 14, but the actual dimensional ratio therebetween is different from the dimensional ratio in FIG. 1.

The subject is a measurement target by the motor function measuring apparatus 12. In this embodiment, the subject is, for example, a biological object such as an animal or a human. The motor function measuring system 10 measures a motor function when the subject is caused to do rapid tapping. More specifically, the subject is instructed to perform a finger tapping motion of repeatedly opening/closing the thumb of a hand and the index finger thereof, and motions of the fingers at this time are measured.

<Motor Function Measuring Apparatus>

The motor function measuring apparatus 12 detects movement information of the subject in time series, and obtains the movement information of the subject relating to at least one of the followings: a distance; a speed; an acceleration; and a jerk, as waveform data.

The motor function measuring apparatus 12 includes motion sensors 22 having a generator coil (a magnetic field generator) that generates a magnetic field and a detector coil (a magnetic field detecting unit) that detects the magnetic field, a motion sensor interface 24, and a motion sensor control unit 26. The motion sensor 22 functions as a sensor for measuring a motor function.

In this case, the motion sensor control unit 26 is arranged on an unillustrated substrate provided inside a housing 28 which is formed in a box shape and serves as a main body. The motion sensors 22 are freely and detachably connected to the housing 28 through first and second connectors 30a and 30b provided at the front face of the housing 28. Also, as will be discussed later, the generator coil is attached to the lower side of the nail portion of the thumb of the subject, and the detector coil is attached to the upper side of the nail portion of the index finger of the subject.

As shown in FIG. 1, provided side by side along the horizontal direction on the front panel of the housing 28 are the first and second connectors 30a and 30b serving as a connecting unit to which respective motion sensors 22 for the right and left hands are attached, a third connector 30c where a wire lead is connected which supplies an output signal by the motion sensor control unit 26 to the motor function analyzing apparatus 14, a fourth connector 30d to which a power source 32 that activates/deactivates the motion sensor control unit 26 is connected, and a switch 34 that turns on/off the motion sensor control unit 26. The first to fourth connectors 30a to 30d may be provided on the rear face or a side face of the housing 28 instead of the front face of the housing 28.

In this case, it is preferable that the first to fourth connectors 30a to 30d should be female connectors, respectively. Also, a casing 36 that configures the housing member 20 is mounted on the top face of the housing 28. In the example case shown in FIG. 1, the housing 28 where the motion sensor control unit 26 is arranged and the casing 36 of the housing member 20 are separate pieces.

Figure 3:
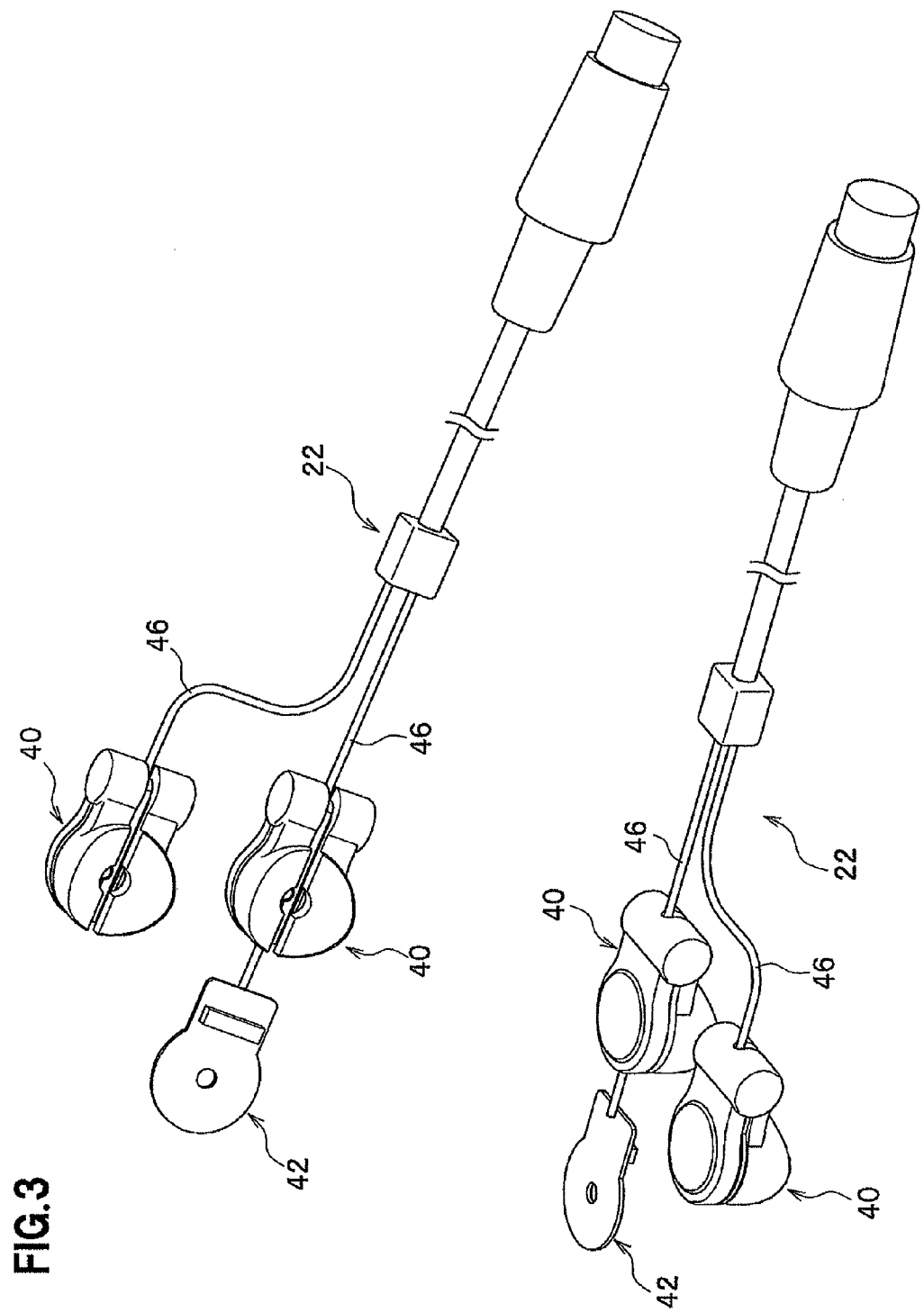
FIG. 3 is a perspective view showing motion sensors for a right hand and a left hand.

FIG. 3 is a perspective view showing respective motion sensors 22 for the right and left hands. As shown in FIG. 3, the motion sensors 22 are a pair of motion sensors 22 with the same configuration for the right and left hands. An explanation will be given of only the motion sensor 22 for the left hand, and the explanation of the motion sensor 22 for the right hand will be omitted.

In this embodiment, the explanation will be given of a case in which portions to which a pair of holders 40 are attached are respective nail portions of the thumb and the index finger. The present invention is not limited to this case, and for example, such holders may be attached to finger portions other than the nail portion. Also, the fingers are not limited to the thumb and the index finger, and the holders 40 can be attached to any finger like a pinky finger. Also, portions where the holders 40 are attached are not limited to the nail portion of the subject and the finger thereof, and for example, may be a periphery portion to a finger like the palm of a hand. Hence, the nail portion of the subject, a finger, and a periphery portion to the finger are set as the portions where the holders 40 are attached.

Figure 4:
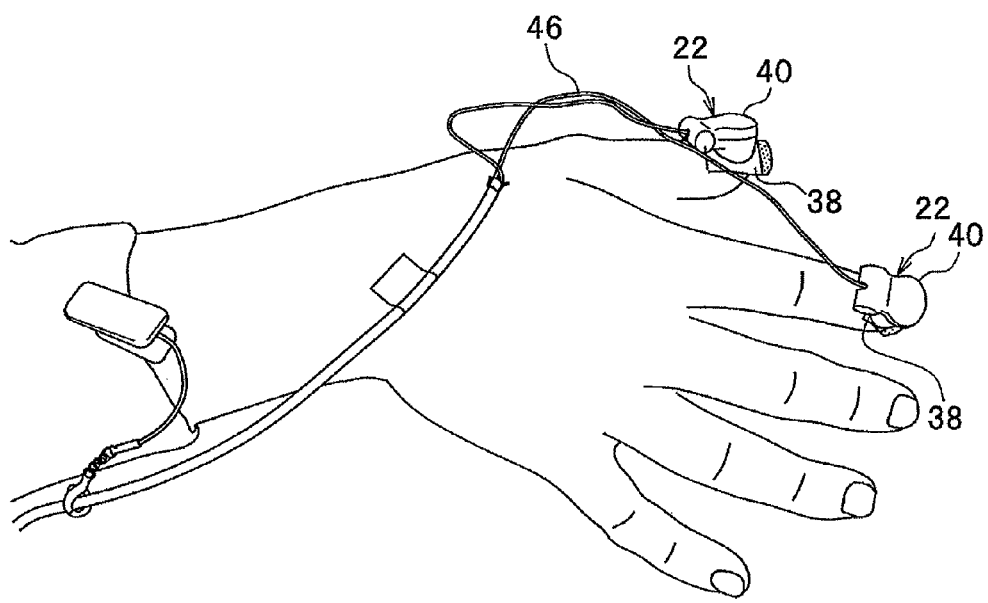
FIG. 4 is a perspective view showing a condition in which a holder is attached to a nail portion of an subject via an adhesive sheet.
Figure 5:
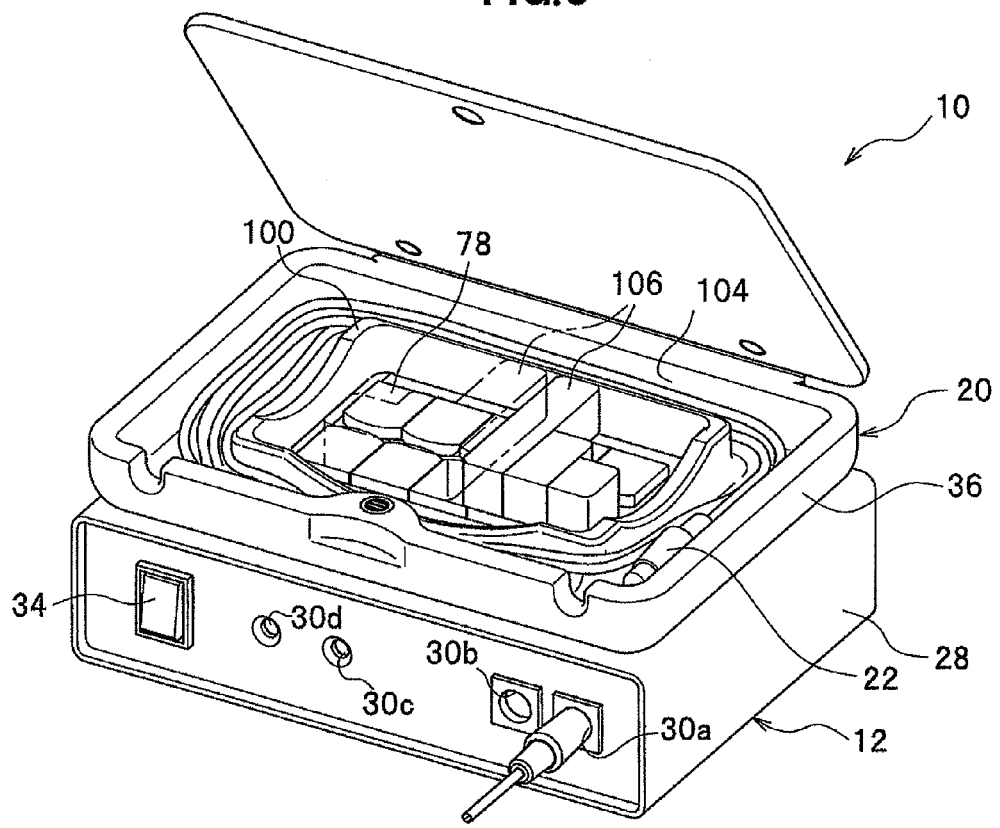
FIG. 5 is a perspective view showing a condition in which various measuring instruments are retained in a casing.

FIG. 4 is a perspective view showing a condition in which the holders 40 are attached to respective nail portions of the subject via adhesive sheets 38. FIG. 5 is a perspective view showing a condition in which various measuring instruments like the motion sensors 22 are housed in the casing 36. A housing space 104 is formed inwardly of an internal wall 100 of the casing 36, and plural stacked adhesive members 78 and a pair of calibration blocks 106 are housed in the housing space 104.

Figure 6:
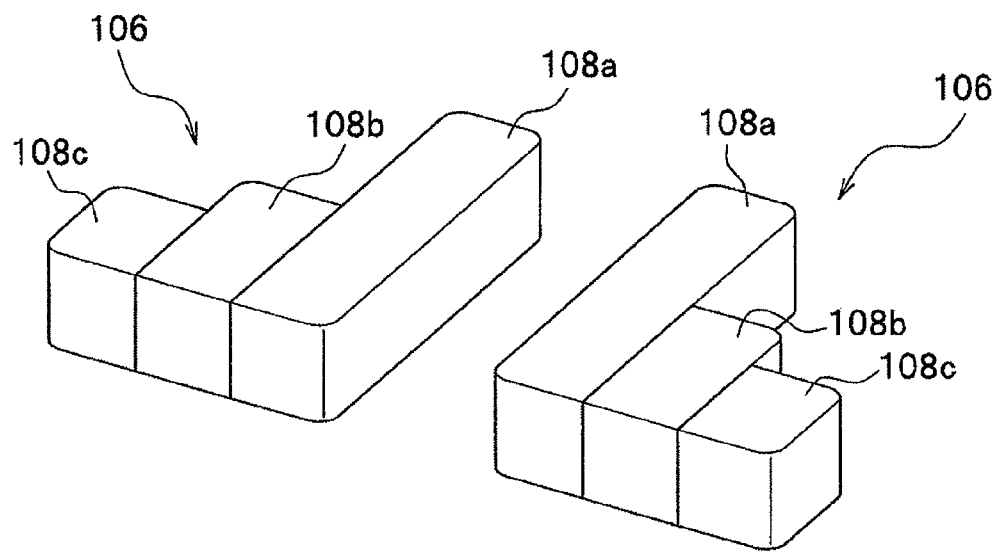
FIG. 6 is a perspective view showing an illustrative configuration of a calibration block.
Figure 7:
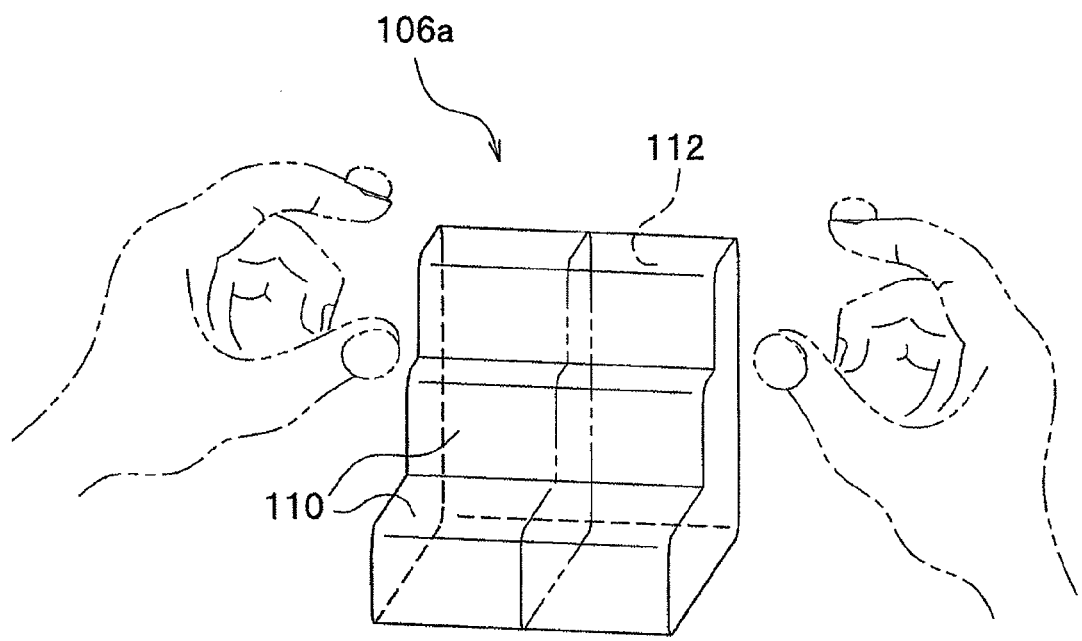
FIG. 7 is a perspective view showing another illustrative configuration of a calibration block.
Figure 8:
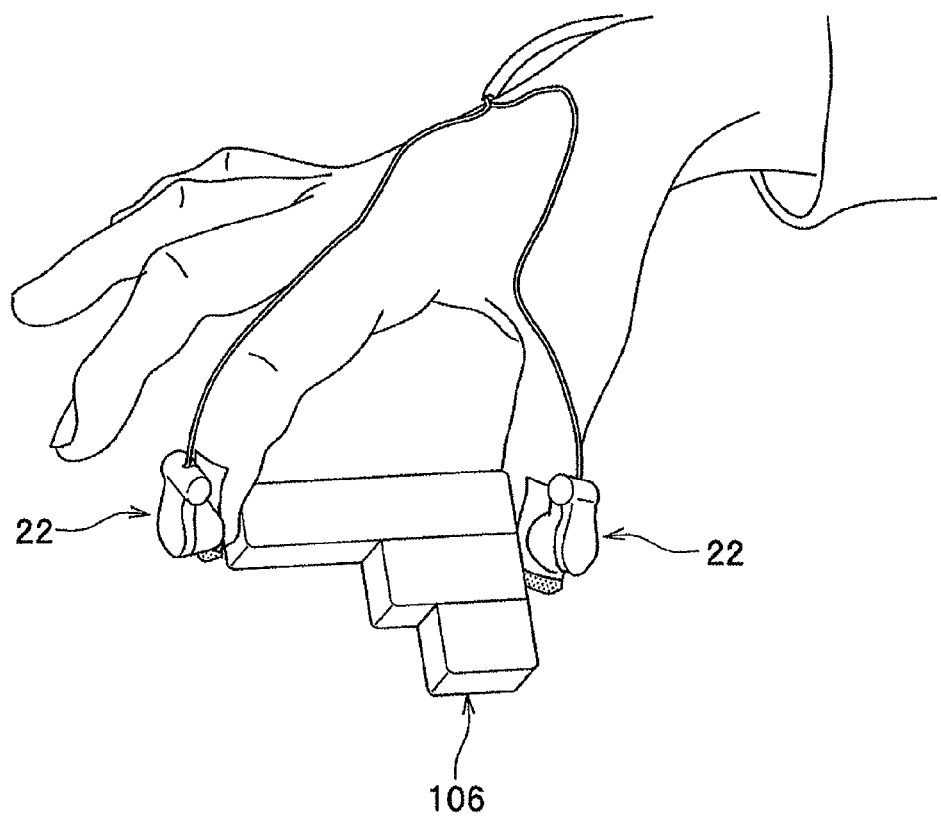
FIG. 8 is a perspective view showing a condition in which a calibration block is held between a thumb and an index finger.

FIG. 6 is a perspective view showing an illustrative configuration of the pair of calibration blocks 106 which are separated in the figure. FIG. 7 is a perspective view showing another illustrative configuration of a calibration block that is a single calibration block 106a in an integral form. FIG. 8 is a perspective view showing a condition in which the calibration block 106 is held between the thumb of the subject and the index finger thereof.

As shown in FIG. 8, the calibration block 106 (106a) is an instrument for obtaining a voltage value at a predetermined distance when the subject holds the calibration block 106 (106a) between the thumb and the index finger, and for performing correction for each subject based on the voltage value (in order to precisely recognize a relationship between a voltage value and a distance between the two fingers) because the fingers have different sizes, etc., subject by subject.

As shown in FIG. 6, two types of the calibration blocks 106 are present; for the right hand, and for the left hand. The calibration block 106 includes three kinds of blocks (first to third blocks 108) having the same width and thickness but different total lengths in the axial line direction, and each block is formed in a substantially cuboidal shape. The three blocks 108 are fixed together and arranged side by side in the direction orthogonal to the axial line direction. For example, the first block 108a, the second block 108b, and the third block 108c have respective total length in the axial line direction set to be substantially 60 mm, substantially 30 mm, and substantially 20 mm, respectively.

In the example case shown in FIG. 6, two calibration blocks 106 which are in line symmetric shape and separated from each other are shown: the calibration block 106 for the right hand; and the calibration block 106 for the left hand. However, a single calibration block 106 may be prepared, and may be used for both right hand and left hand by reversing (turning back) the front and rear faces.

Also, as shown in FIG. 7, a single calibration block 106a which is in a stepped shape 110 with plural steps (in this embodiment, three steps) at one side, and is in a planar shape 112 at another side that is the opposite side of the stepped shape 110 may be used in order to obtain calibration data. At this time, it is appropriate if respective thumbs of the right hand and the left hand are located at the stepped-shape-110 side, respective index fingers of the right hand and the left hand are located at the planar-shape 112 side, and the calibration block 106a may be held between the thumbs of both hands and the index fingers of both hands for each step of the stepped shape 110. Although the calibration blocks 106, 106a employ a multi-step structure, it is not necessary to use each step for a calibration.

When the pair of calibration blocks 106 in a separate configuration are prepared, or when the single calibration block 106a with the multi-step shape 110 is prepared, there is an advantage that both pieces of calibration data for the right hand and the left hand of the subject can be obtained simultaneously. When pieces of calibration data for both hands of the subject are obtained simultaneously, it is possible to suppress the interference of the motion sensor 22 for the right hand and the motion sensor 22 for the left hand by spacing apart respective fingers of the right hand and the left hand by a predetermined distance.

In addition to a case in which the calibration block 106 (106a) is used, calibration data of the subject can be obtained by using, for example, other devices like a calibration data detecting device with a variable resistor.

Figure 9:
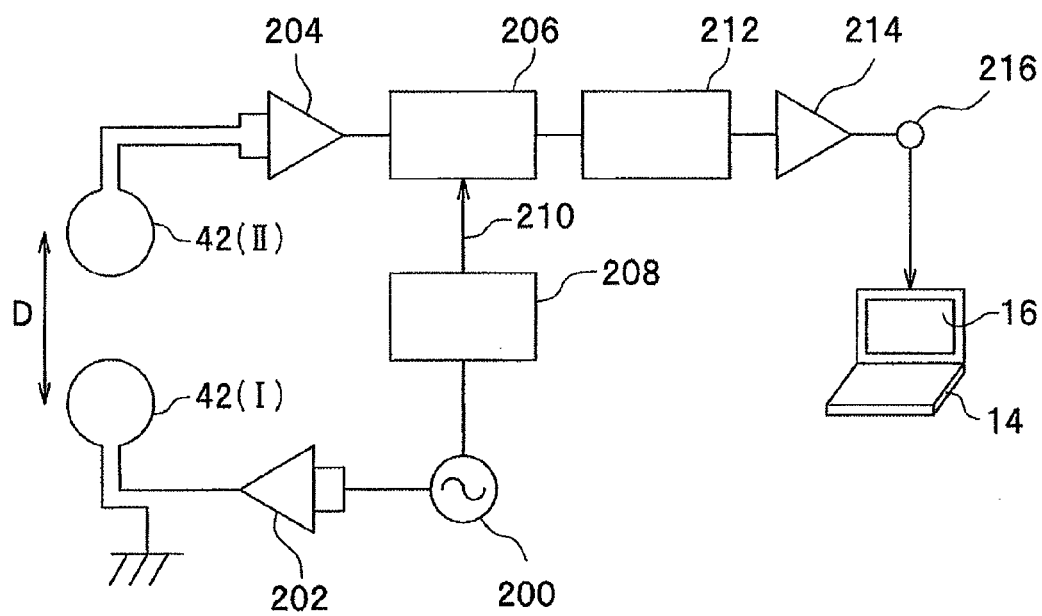
FIG. 9 is a block diagram showing a configuration of a motion sensor control unit.

FIG. 9 is a block diagram showing a configuration of the motion sensor control unit 26 (see FIG. 2). An explanation will be given of the procedures how the motion sensor control unit 26 obtains waveform data.

As shown in FIG. 9, an AC generator circuit (an AC current supplying unit) 200 generates an AC voltage with a certain frequency (e.g., 20 kHz). The AC voltage with a certain frequency generated by the AC generator circuit 200 is amplified by a current-generating amplifier circuit 202, and an AC current amplified by the current-generating amplifier circuit 202 is caused to flow through a generator coil in a coil substrate 42(I). A magnetic field generated by the generator coil in the one coil substrate 42(I) generates an induced electromotive force in a detector coil in another coil substrate 42(II).

The generated induced electromotive force (that has the same frequency as that of the AC voltage with a certain frequency generated by the AC generator circuit 200) is amplified by a pre-amplifier circuit 204, and a signal having undergone amplification is input into a wave detector circuit 206. The wave detector circuit 206 performs wave detection at the certain frequency generated by the AC generator circuit 200 or at a double frequency. Hence, an output by the AC generator circuit 200 has a phase adjusted by a phase adjuster circuit 208, and a reference signal 210 thereof is input into a reference-signal input terminal of the wave detector circuit 206.

When wave detection is performed at a double frequency of the certain frequency, the phase adjuster circuit 208 is not always requisite. As a simple circuit configuration of performing wave detection at the double frequency, it is appropriate if the certain frequency of the AC generator circuit 200 is set to be twice, the frequency is converted into a half frequency by a frequency divider, and a voltage is input into the current generating amplifier circuit 202, and a signal having a frequency twice as much as the certain frequency of the AC generator circuit 200 may be input as the reference signal 210 into the reference-signal input terminal of the wave detector circuit 206.

An output signal by the wave detector circuit 206 passes through an LPF (Low-Pass Filter) circuit 212, is amplified by an amplifier circuit 214 in order to obtain a desired voltage, and is input into the motor function analyzing apparatus 14. An output signal 216 by the amplifier circuit 214 is a voltage corresponding to a relative distance D between the generator coil and the detector coil attached to the thumb and the index finger, respectively. Note that the wave detector circuit 206, the LPF circuit 212 and the amplifier circuit 214 serve as detected signal processing units, respectively.

The explanation was given of a case in which the magnetic-sensor-type motion sensor 22 is used, but the kind of the motion sensor 22 is not limited to any particular one as long as it can measure a motion through generation of a magnetic field. For example, conventionally well-known strain gauge and acceleration sensor may be used.

<Motor Function Analyzing Apparatus>

As shown in FIG. 2, the motor function analyzing apparatus 14 records and analyzes data measured by the motor function measuring apparatus 12. The motor function analyzing apparatus 14 includes a data input unit 320 where an output signal by the motion sensor control unit 26 is supplied, a control unit 330, a movement waveform generating unit 302, a signal control unit 303, an subject information processing unit 304, an output processing unit 306, and a memory 310.

In this embodiment, a term movement waveform means time-series data of a distance value between the two fingers, and as long as it is mentioned, includes at least one of the followings: a distance waveform; a speed waveform; an acceleration waveform; and a jerk waveform.

The control unit 330 inputs an output signal supplied from the data input unit 320 into the movement waveform generating unit 302, and outputs movement waveform obtained from the movement waveform generating unit 302 and subject information obtained from the subject information processing unit 304 to the display unit 18, i.e., is the unit which inputs/outputs data from various units. The motor function analyzing apparatus 14 includes a CPU (Central Processing Unit), a ROM (Read Only Memory), a RAM (Random Access Memory), a hard-disk drive, and the like. The process by the control unit 330, etc., is realized by the CPU reading a program from the memory 310 and executing an arithmetic processing.

<Movement Waveform Generating Unit>

As shown in FIG. 2, voltage data supplied from the motor function measuring apparatus 12 is sent to the movement waveform generating unit 302 through the control unit 330. The movement waveform generating unit 302 includes a calibration-point measuring unit 3021, a conversion-formula generating unit 3022, a movement-waveform converting unit 3023, and a movement-waveform differentiation unit 3024. Explanations will be given of the four units, respectively.

The calibration-point measuring unit 3021 measures three calibration points. The calibration point is a combination (D, V) of a distance value D between the cushion of the thumb and that of the index finger and a voltage value D output by the motor function measuring apparatus 12 when the distance D between the two fingers is maintained. The three calibration points obtained by the calibration-point measuring unit 3021 are used for generating a conversion formula that converts a voltage value into a distance value in the conversion-formula generating unit 3022. Hereinafter, an explanation will be given of how to calculate three calibration points (see a calibration point (0) (D0, V0) in FIG. 13, a calibration point (1) (D1, V1), and a calibration point (2) (D2, V2)) as an example case.

Figure 10:
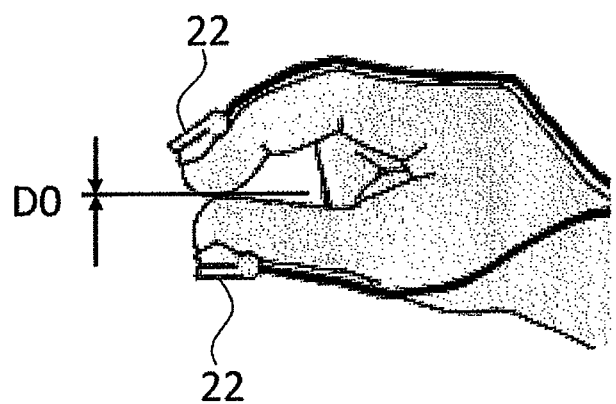
FIG. 10 is a diagram showing how a calibration point unique to each subject is measured.

A voltage value V0 of the calibration point (0) (D0, V0) is a voltage value obtained when the subject slightly touches the thumb to the index finger as shown in FIG. 10. At this time, because respective cushions of the two fingers are contacting with each other, a distance value D0 is 0 mm. When setting is made so that a distance value D0=0 mm, as will be discussed later, the precision of a distance value when the two fingers contact in a conversion formula calculated by the movement-waveform converting unit 3023 becomes high. When the precision of the distance value when the two fingers are contacting is high, a contact determination is facilitated, and it becomes easy to calculate a contacting time, etc., of the two fingers during a finger tapping motion. Setting is made so that D0=0 mm in this embodiment, but such setting may be made to other values closer to D0=0 mm.

Figure 11:
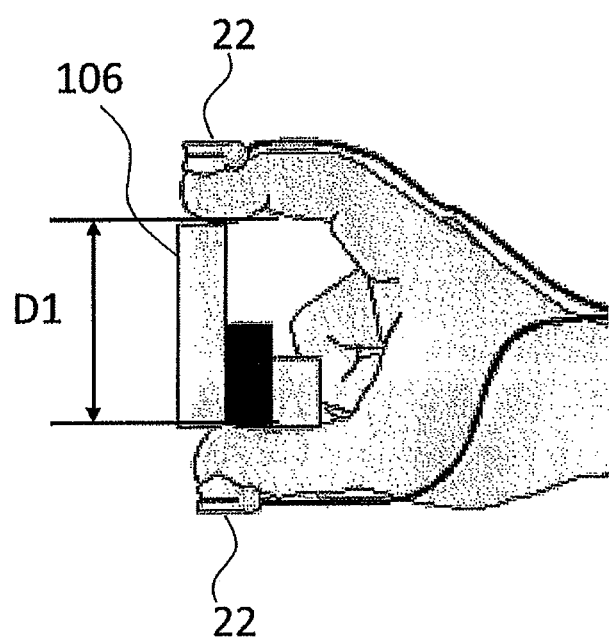
FIG. 11 is a diagram showing how a calibration point unique to each subject is measured.

Next, a voltage value V1 of a calibration point (1) (D1, V1) is measured when the subject holds the first block 108a (60 mm) of the calibration block 106 between the thumb and the index finger as shown in FIG. 11. Because the distance between respective cushions of the two fingers is equal to the block length, setting is made so that a distance value D1=60 mm. In addition, D1 (the block length) may not equal to 60 mm if D1 is greater than D0 and is smaller than a distance between respective cushions of the two fingers when the subject opens the two fingers at a maximum. That is, the second block 108*b* or the third block 108*c* may be used, and blocks with other appropriate lengths may be used. Also, calibration may be performed using a scale or a bar with a predetermined length instead of using the calibration block 106.

Also, the precision can be improved by setting a limit to the value of D1 as follows. As shown in FIG. 31A1, it is desirable that a distance between respective cushions of the two fingers should be measured (a distance value at this time is set to be D1*a*) when respective fingertips of the two fingers during a finger tapping operation are in a condition substantially parallel at a maximum, and this distance value should be set to be the value of D1. The reasons why the precision improves when setting D1 in this fashion are the following two reasons.

First, this is because a voltage obtained from the detector coil becomes toughest relative to a varying in the angular direction of the coil when the generator coil and the detector coil are in a positional relationship parallel to each other. The detail of this phenomenon will be explained with reference to FIGS. 32A to 32E. As shown in FIG. 32A, a generator coil 3202 is fixed and a detector coil 3201 is positioned at a distance apart from the center of the generator coil 3202 in the central axis direction by the distance D1. With the inclination between the center axis of the generator coil 3202 and that of the detector coil 3201 being θ, θ is changed within a range from 0 to 360 degrees. The plotted graph of the upper part of FIG. 32B indicates a relationship between a magnetic field intensity detected by the detector coil 3201 and θ.

As is indicated by this graph, the magnetic field intensity becomes maximum when θ=0 degree. When θ=60 degrees, the magnetic field intensity decreases to substantially 60 percent of one when θ=0 degree, and the magnetic field intensity becomes zero when θ=90 degrees. Respective layouts of the two coils in respective cases are shown in FIGS. 32C, 32D, and 32E. Also, the graph of the upper part of FIG. 32B is differentiated in order to obtain a graph of a change rate of the magnetic field intensity, which is shown in the graph of the lower part of FIG. 32B. As can be seen in this graph, the change level of the magnetic field intensity relative to the change in the angle between the coils becomes 0 when θ=0 degree. The change level of the magnetic field intensity also becomes 0 when θ=180 degrees, but it is a rare case in which the detector coil is reversed during a finger tapping motion, so that such a rare case is not taken into consideration. As is clear from the above explanation, when an angle between the two fingers changes during a calibration measurement, an error is not likely to be generated in the magnetic field intensity.

Next, the second reason why setting is made so that D1=D1*a* will be explained. When setting is made so that D1=D1*a*, respective postures of the two fingers when holding the calibration block 106 become natural postures like the finger tapping motion, so that an error is not likely to be generated during a calibration measurement. A detail of this reason will be explained below.

As shown in FIG. 31A1, a distance between respective cushions of the two fingers is measured when the two fingers become substantially parallel at a maximum during the finger tapping motion, and D1*a* is obtained. When calibration measurement is made using the portion of the calibration block corresponding to the length D1*a*, as shown in FIG. 31A2, the calibration block can be held in natural postures like ones during the finger tapping motion. Accordingly, when the calibration block is held in natural postures like ones during the finger tapping motion, a voltage value during the finger tapping motion is not likely to differ largely from a voltage value during a calibration measurement. Hence, the precision of a conversion formula calculated by the movement-waveform converting unit 3023 becomes high.

However, when D1<D1*a* as shown in FIG. 31B and when D1>D1*a* as shown in FIG. 31C, the two fingers are not parallel to each other during the finger tapping motion. Hence, when a parallel plane of the calibration block is held during a calibration measurement, respective fingertips of the thumb and the index finger are bent along the parallel plane of the calibration block, and become different postures from the natural finger postures during the finger tapping motion. The positional relationship between the two coils and the angular relationship therebetween also become different from ones during the finger tapping motion, so that a voltage value during the finger tapping motion becomes largely different from a voltage value during a calibration measurement. As a result, the precision of a conversion formula calculated by the movement-waveform converting unit 3023 decreases. In order to avoid such a problem, it is appropriate to measure the distance value D1*a* when the two fingers are substantially parallel to each other at a maximum during the finger tapping motion, and to set the block length D1 to be D1*a*. In this embodiment, D1*a* is defined as a distance value when the two fingers are substantially parallel at a maximum during the finger tapping motion, but a similar value to D1*a* may be set as D1.

The voltage value V0 of the calibration point (0) and the voltage value V1 of the calibration point (1) depend on the shapes of the fingers of the subject, and how to attach the motion sensors 22 thereto, etc., so that those values are unique to each subject. Accordingly, when the subject changes or when the motion sensors 22 are attached again, it is desirable to measure the voltage values V0 and V1 again for each occasion. When the voltage values V0 and V1 are measured again for each occasion, the precision of a conversion formula obtained from the conversion-formula generating unit 3022 improves.

Figure 12:
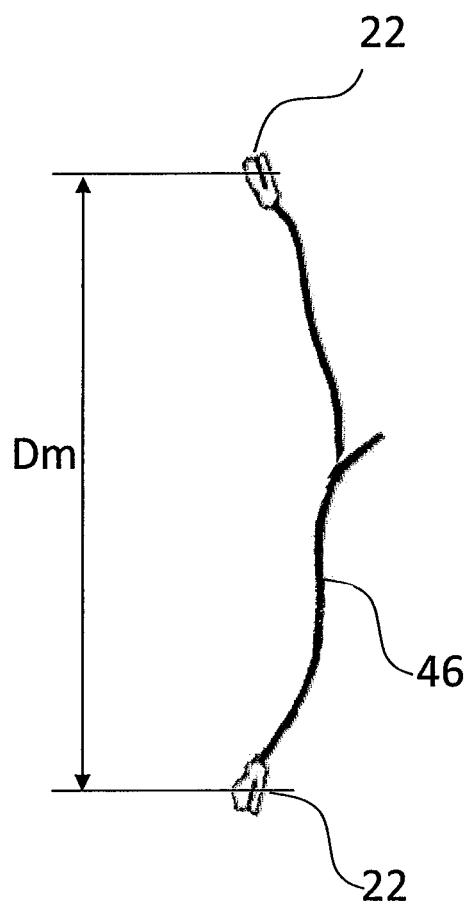
FIG. 12 is a diagram showing how a calibration point unique to each apparatus is measured.

Eventually, a voltage value V2 of the calibration point (2) (D2, V2) is a voltage value obtained when the detector coil of the motion sensor 22 and the generator coil thereof are located most distant from each other within the restriction of the wire lead 46 (see FIG. 12), as is indicated by a following formula (1). The detail of the formula (1) will be discussed later.

$$D'=\alpha(V-\gamma)^{-1/3}+\beta \qquad (1)$$

When the detector coil and the generator coil are located most distant from each other, a condition in which the detector coil detects no magnetic field can be approximately produced. This makes it possible to obtain unique offset voltage value to each apparatus.

As explained above, because V2 is a voltage value unique to each apparatus, when such a voltage value is once measured before the apparatus is used, it becomes unnecessary to measure such a voltage value again thereafter. Information on the calibration point (2) is stored in the memory 310 of the control unit 330 or an external memory beforehand.

The method for measuring V2 is not limited to the above-explained method as long as a condition in which no magnetic field is detected can be approximately generated by the method. For example, as shown in FIG. 32E, a method of measuring a voltage value while adjusting the angular relationship between the two coils so that no magnetic force enters in the detector coil, such as arranging the two coils so that the center axis of the generator coil is orthogonal to the center axis of the detector coil is possible. A method of directly measuring the offset voltage of the circuit is also possible.

Also, it is preferable if V2 is measured beforehand through an option screen shown in FIG. 23 which will be discussed later. The distance value D2 is set to be an actual measured value Dm (see FIG. 12) between the two coils when the two coils of the motion sensor 22 are located most distant from each other. Alternatively, an appropriate value may be set as D2 beforehand (in this embodiment, 300 mm). The value of D2 is not limited to 300 mm as long as it is sufficiently larger than a distance between the cushions of fingers when the subject opens the two fingers at a maximum. The value of D2 may be unrelated to the measurement method of V2.

Next, the conversion-formula generating unit 3022 (see FIG. 2) calculates, using the three calibration points (the calibration point (0) (D0, V0), the calibration point (1) (D1, V1), and the calibration point (2) (D2, V2)) obtained by the calibration-point measuring unit 3021, a conversion formula that converts a voltage value supplied from the motor function measuring apparatus 12 into a distance value.

Figure 13:
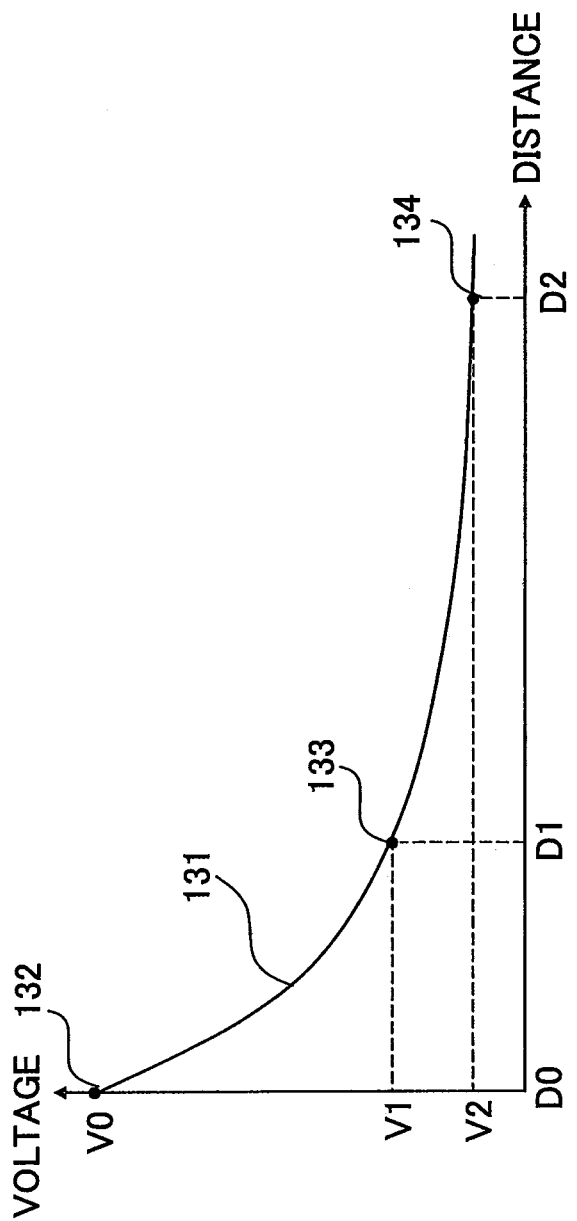
FIG. 13 is a graph showing a relationship between a voltage and a distance.

The conversion formula obtained by the conversion-formula generating unit 3022 is indicated in FIG. 13 as a conversion curve 131. In order to obtain the conversion curve 131, constants $\alpha$, $\beta$, and $\gamma$ are calculated by substituting the three calibration points into the above-explained formula (1) and by solving simultaneous equations including three equations. D in the formula (1) indicates a distance between the two fingers, and V indicates a voltage value output by the apparatus. A conversion formula that converts a voltage value into a distance value can be obtained when the obtained $\alpha$, $\beta$, and $\gamma$ are substituted into the formula (1). As explained above, FIG. 13 shows a curve of the calculated conversion formula (the conversion curve 131) and the calibration points (0), (1), and (2). A distance value can be calculated highly precisely from a voltage value at distances other than the distances D0, D1, and D2 where the calibration points (0), (1), and (2) are present, respectively.

The explanation was given of the method of calculating the conversion formula using the three calibration points. That is, the calibration-point measuring unit 3021 includes an apparatus-unique-voltage measuring unit that measures a voltage unique to each apparatus with the magnetic field generator and the magnetic field detector being kept in a condition apart from each other by a predetermined distance, and an subject-unique-voltage measuring unit that measures a voltage unique to each subject with the two predetermined portions of the biological object where the magnetic field generator and the magnetic field detector are attached being kept in a condition apart from each other by the predetermined distance.

In this embodiment, the calibration-point measuring unit 3021 measures the two calibration points (the calibration points (0) and (1)) unique to each subject and the calibration point (the calibration point (2)) unique to each apparatus. However, when both calibration point unique to each apparatus and the calibration points unique to each subject are used, the number of calibration points may be other number than 3.

Next, the movement-waveform converting unit 3023 (see FIG. 2) substitutes time-series data of a voltage value supplied from the motor function measuring apparatus 12 into the conversion formula obtained by the conversion-formula generating unit 3022 in order to convert the time-series data into a movement waveform.

When a method of causing the conversion-formula generating unit 3022 to calculate the conversion formula using the three calibration points is applied, there are two advantages. The first advantage is that a measurement can be easily carried out with a little number of calibrations. The reason of this advantage will be explained with reference to FIGS. 14A and 14B below.

Figure 14A:
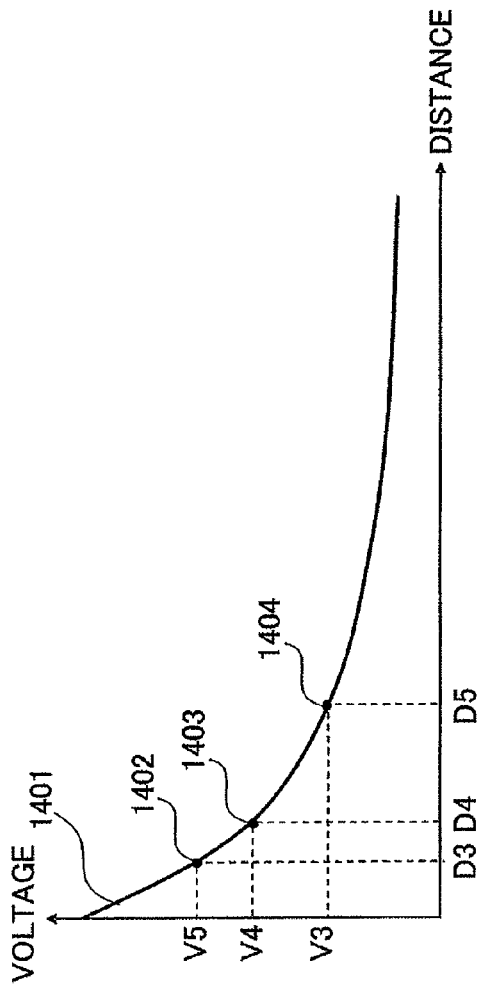
FIG. 14A is a diagram for explaining a conventional scheme, and is a graph showing a relationship between a voltage and a distance.

According to a conventional scheme, the above-explained formula (1) is used which is an approximate curve representing the relationship between the voltage value V and the distance D between the two fingers, and a calibration point is measured for each subject in order to adjust parameters. In order to obtain the parameters $\alpha$, $\beta$, and $\gamma$ of this formula, at least three calibration points are requisite, so that three calibration points (a calibration point (3) 1402 (D3, V5), a calibration point (4) 1403 (D4, V4), and a calibration point (5) 1404 (D5, V3)) shown in FIG. 14A are measured for each time before a measurement. Hence, according to the conventional scheme, setting is made so that D3=20 mm, D4=30 mm, and D5=60 mm.

As explained above, because three kinds of calibration measurements are requisite for each time before a measurement according to the conventional scheme, it takes a time to start measurement. Also, three blocks are requisite, so that production, management, and storage of the calibration blocks require an effort. According to this embodiment, however, the number of calibration points necessary to measure before a measurement for each time is two (a calibration point (0) 132 and a calibration point (1) 133 shown in FIG. 13), so that a time necessary for a calibration measurement can be shortened.

In this fashion, by measuring a calibration point (2) 134 before the apparatus is used, the number of calibration points necessary before a measurement can be reduced. Also, the number of calibration points needing the calibration block is one (the calibration point (1) 133), so that preparation of one kind of calibration block is sufficient. Hence, production, management, and storage of the calibration block become simplified. As is clear from the above explanation, this embodiment can overcome the problem inherent to the conventional scheme.

Next, the second advantage of this embodiment is that a voltage value can be converted into a distance value more precisely than the conventional scheme. According to the conventional scheme, the precision of a distance value calculated from a voltage value largely depends on the precision of the calibration point. This problem of the conventional scheme will be explained with reference to FIG. 14B, and the reason why this embodiment can overcome such a problem will be explained successively.

Figure 14B:
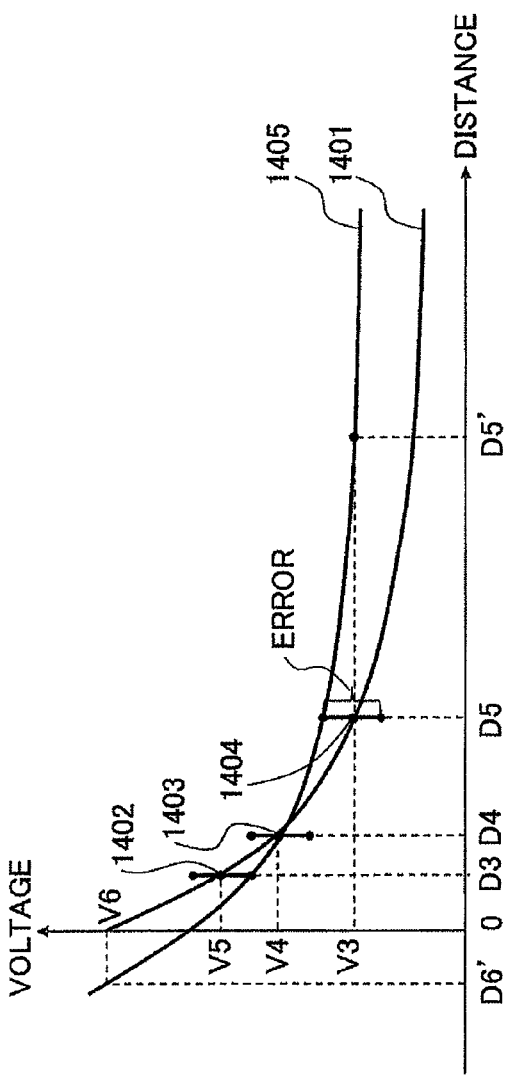
FIG. 14B is a diagram for explaining a conventional scheme, and is a graph showing a relationship between a voltage and a distance.

It is presumed that a conversion curve A1401 is obtained when the calibration point includes no error as shown in FIG. 14B. The conversion curve A1401 passes through the calibration point (3) 1402, the calibration point (4) 1403, and the calibration point (5) 1404.

However, according to an actual measurement of a calibration point, an error is often generated in the calibration point because of holding of the calibration block 106 with the two fingers standing up, or holding it strongly, so that it is not always true that a conversion curve A is calculated. For example, when a negative error is generated in the calibration point (3) 1402, and a positive error is generated in the calibration point (5) 1404, a conversion formula B1405 is obtained. In FIG. 14B, lines running over and below the calibration points (3) 1402, (4) 1403, and (5) 1404 represent a rough range of an error of a voltage value generated at respective points.

When a voltage value is converted into a distance value using this conversion curve B1405, the distance value includes a large error. For example, when a voltage value V3 in FIG. 14B is converted into a distance value, it is converted into an actual distance value D5 through the conversion curve A1401, but is converted into a distance value D'5 through the conversion curve B1405, which is largely different from the actual distance value D5. Also, when a voltage value V6 in FIG. 14B is converted into a distance value, it is converted into an actual distance value 0 through the conversion curve A1401, but is converted into a distance value D'6 through the conversion curve B1405, which is smaller than the actual distance value 0. As is clear from the above explanation, according to the conventional scheme, the error of the calibration point is amplified at a location apart from the calibration point (where the distance is equal to or longer than D3 but is equal to or shorter than D5), so that a distance value includes a large error.

On the other hand, according to the method of this embodiment, the precision of the conversion curve is not likely to depend on the error in the calibration point. This is because ends of the conversion curve do not largely vary since the calibration points are located at three points: the left end; the center; and the right end of the conversion curve. According to the conventional scheme, the calibration points (3), (4), and (5) are collectively located around the center of the conversion curve, so that when those calibration points include an error, such an error is amplified in the vicinity of the right and left ends of the conversion curve.

Figure 15:
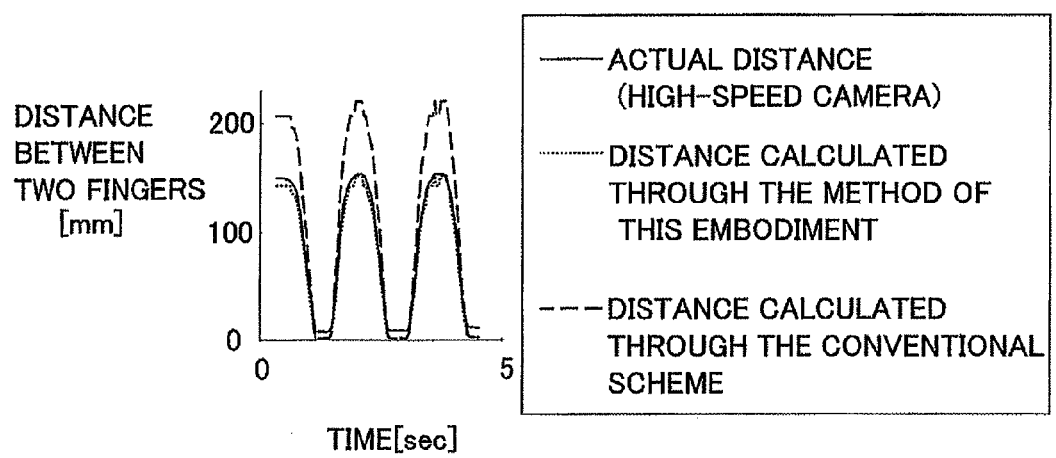
FIG. 15 is an exemplary diagram showing how a distance between two fingers changes with time.

FIG. 15 is an exemplary diagram for comparing a distance between the two fingers in the finger tapping motion calculated through the conventional scheme with a distance between the two fingers in the finger tapping motion calculated through the method of this embodiment. The thick line indicates an actual distance value obtained from an image picked up by a high-speed camera. The dotted line indicates a distance value calculated through the method of this embodiment and the dashed line indicates a distance value calculated through the conventional scheme. As is indicated in the figure, the distance value calculated through the conventional scheme has a large difference from the actual value, but the distance value calculated through the method of this embodiment is proximate to the actual value.

Next, the movement-waveform differentiation unit 3024 (see FIG. 2) performs time differentiation or time integration on the converted movement waveform in order to complementarily generate a distance waveform, a speed waveform, an acceleration waveform, and a jerk waveform.

<Subject Information Processing Unit>

The subject information processing unit 304 (see FIG. 2) includes an subject DB (Data Base) in the memory 310 that stores subject information, information on an analysis result, etc., and manages information to be recorded in the subject DB.

More specifically, the subject information processing unit 304 performs generally four processes: (1) registers, corrects, deletes, searches, and sorts subject information; (2) associates subject information with measurement data; (3) registers, corrects, and deletes an analysis result of measurement data (adds, corrects, and deletes items); and (4) registers, corrects, and deletes a processed result of a statistical process when such statistical process was executed, together with the subject DB.

Examples of the subject information registered in the subject DB are an subject ID (Identifier), a name, birth date, age, height, weight, the name of disease, and a comment on the subject. Information management by such subject information processing unit 304 can be easily realized by a conventionally well-known program and data structure.

<Output Processing Unit>

The output processing unit 306 causes the display unit 18 to display the subject information, information on an analysis result, etc., registered in the subject DB in a display form easily understandable visually which uses a graph, a table, etc., as needed. It is not necessary for the output processing unit 306 to display all analysis results simultaneously, and the output processing unit 306 may be configured to display only items selected by a user accordingly.

<Display Unit>

The display unit 18 displays the subject information obtained from the subject information processing unit 304 and a movement waveform obtained from the movement-waveform generating unit 302, and is realized by, for example, an LCD (Liquid Crystal Display) or a CRT (Cathode Ray Tube) display, and a printer.

<Operation Input Unit>

The operation input unit 16 is for the user of the motor function measuring apparatus 12 to input subject information, and is realized by, for example, a keyboard and a mouse. When subject information is input, as a user interface that assists the input by the user, an input screen may be displayed on the display.

<Illustrative Screens>

Next, an explanation will be given of illustrative screens displayed by the motor function measuring system 10 according to this embodiment with reference to FIGS. 16 to 24. These screens are displayed on the display unit 18 in accordance with an instruction given from the output processing unit 306 of the motor function analyzing apparatus 14 to the display unit 18.

FIG. 16 shows an illustrative screen (a measurement-data-list screen 2700 (a control screen)) of a list of measurement data on a main screen. As shown in FIG. 16, the measurement-data-list screen 2700 includes a measurement-data-list field 2702, a search condition input field 2704, service (function) buttons 2706, and screen switching buttons 2708. In the case of FIG. 16, "measurement data" is selected through the screen switching buttons 2708, and the measurement-data-list screen 2700 is displayed. When an application of this screen display is launched, the measurement-data-list screen 2700 may be initially displayed.

Displayed on the measurement-data-list field 2702 are an "subject ID", a "name", a "measurement date", a "measurement time", a "measurement period", a "measurement method", an "age", a "sex", a "first comment", and a "second comment". Displayed on the search condition input field 2704 are the "subject ID", the "name", the "sex", the "age", the "measurement date", the "measurement method", the "first comment", and the "second comment" as items for searching, and those are inputtable or selectable. When the user of the motor function analyzing apparatus 14 (hereinafter, simply referred to as a "user") inputs or selects any one of those items or a combination thereof, it becomes possible to execute searching. A search result is displayed on the measurement-data-list field 2702.

The service buttons 2706 includes respective buttons (operators) of, as services, new measurement 2720 (first operator) (to create new subject information and to measure a finger tapping), measurement 2722 (first operator) (to measure a finger tapping related to an subject already selected), data analysis 2724 (second operator) (to display analysis information on data selected in the measurement-data-list field 2702), interannual display 2726 (third operator) (to display an interannual graph selected in the measurement-data-list field 2702), "measurement-information delete" (to delete data selected in the measurement-data-list field 2702), and "export" (to output an analysis result of data selected in the measurement-data-list field 2702 in a CSV (Comma Separated Values) format). When such buttons are selected, corresponding functions are activated.

The data analysis button 2724, the interannual display button 2726, the "measurement-information delete" button, and the "export" button are for processes for data selected in the measurement-data-list field 2702. However, when none is selected or when the selected data is already deleted, an error message may be displayed. Also, when the search results exceed 1000 results, a display confirmation message may be displayed.

The service buttons 2706 include, as tools, buttons of "data management" (to edit data selected in the measurement-data-list field 2702) and "option" (to set default values of each screen), and an "end" button (to end this application program) arranged at the lowermost location.

FIG. 17 is an example of a screen of a list of subject data (subject-data-list screen) in the main screen. As shown in FIG. 17, the subject data list screen includes an subject-data-list field 2802, a search condition input field 2804, service (function) buttons 2806 and screen switching buttons 2708. In the case of FIG. 17, "subject data" is selected through the screen switching buttons 2708, and the subject-data-list screen is displayed.

Displayed on the subject-data-list field 2802 are an "subject ID", a "name", "birth date", "sex", a "dominant hand", and a "memo". Displayed on the search condition input field 2804 are the "subject ID", the "name", and "sex" as items for searching, and those are inputtable or selectable. When the user inputs or selects any one of such items or a combination thereof, it becomes possible to execute searching. When a button of "start searching" is operated, searching starts and when a button of "clear condition" is operated, searching conditions set are collectively cleared.

The service buttons 2806 include buttons of, as services, new measurement 2720 (first operator) and measurement 2722 (first operator). Those functions are same as those of the measurement-data-list screen (see FIG. 16), so that duplicated explanation thereof will be omitted.

FIG. 18 shows an illustrative screen for subject information setting. The subject-information setting screen is launched upon operation of the button of new measurement 2720 (see FIG. 16) in the main screen. As shown in FIG. 18, displayed on the subject-information setting screen are an "subject ID", a "name", "birth date", "sex", a "dominant hand", and a "memo", and those are inputtable or selectable. It is desirable that some of such items, such as the "subject ID", and the "name" should be requisite items (an error message is displayed if not input).

The subject-information setting screen has, at the bottom portion thereof, buttons of "obtain information based on an subject ID" (to obtain subject information registered in the subject DB based on an ID input in the field of "subject ID"), "save" (to save the setting and display a setting screen for a measurement (see FIG. 19)), and "close" (to close the subject-information setting screen and to return to the main screen (see FIGS. 16 and 17)).

Figure 19:
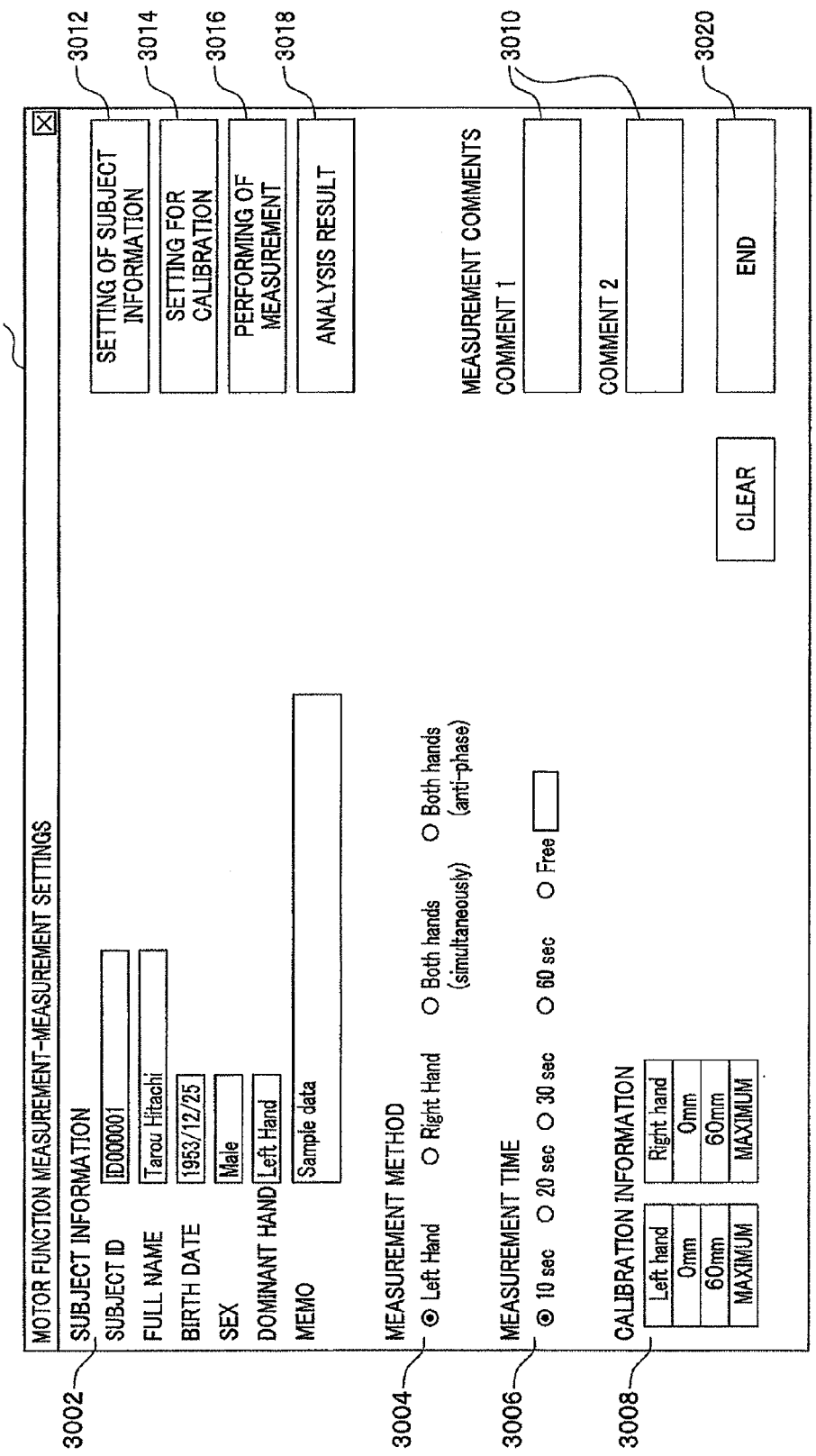
FIG. 19 is a diagram showing an illustrative measurement setting screen.

FIG. 19 shows an illustrative setting screen for a measurement. A measurement setting screen 3000 (a measurement-condition setting screen) is launched upon operation of the button of measurement 2722 (see FIG. 16) in the main screen. As shown in FIG. 19, the measurement setting screen 3000 includes various information fields of an subject information 3002, a measurement method 3004, a measurement time 3006 in order to set a measurement time. When ("option" is selected, a text box becomes inputtable, and a numeral from 1 to 999 can be specified), a calibration information 3008 (displays 0 mm, 60 mm, and the maximum of each executed condition. When no measurement is executed, the background color becomes gray. When measurement was executed, the background color becomes white), and a measurement comment 3010, and buttons of subject information setting 3012, calibration setting 3014, execute measurement 3016, analysis result 3018, and end 3020 (to close the measurement setting screen 3000 and to return to the main screen (see FIGS. 16 and 17)).

When the button of subject information setting 3012 is operated, the subject-information setting screen (see FIG. 18. The display of the button of "save" can be changed to a button of "update") is displayed, and setting (updating) of various pieces of information in the subject information 3002 is enabled. An explanation will be given of a case in which the button of calibration setting 3014 is operated with reference to FIGS. 20A to 21.

Figure 20A:
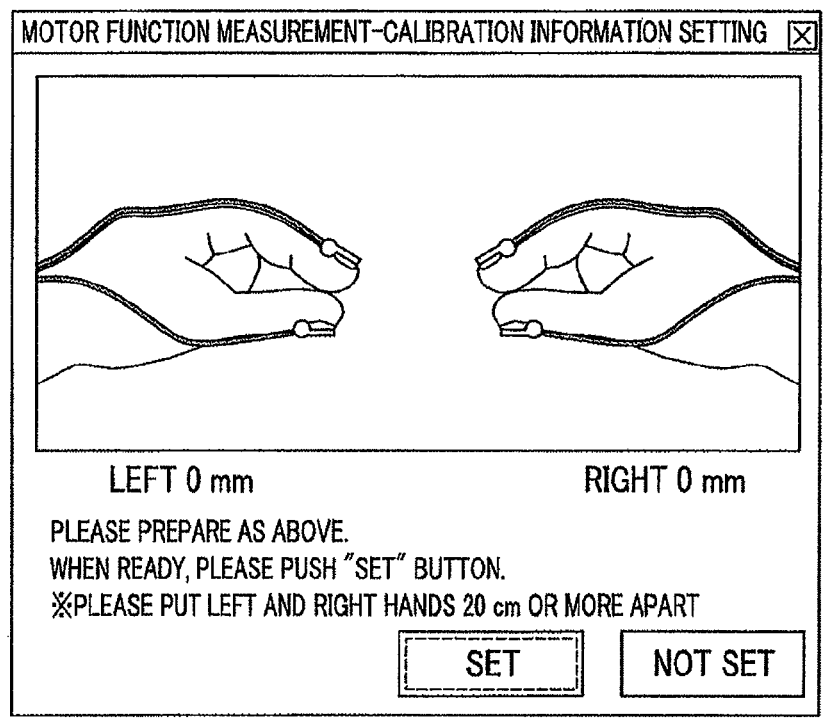
FIG. 20A is a diagram showing an illustrative screen launched when a button for setting a calibration is operated.
Figure 20B:
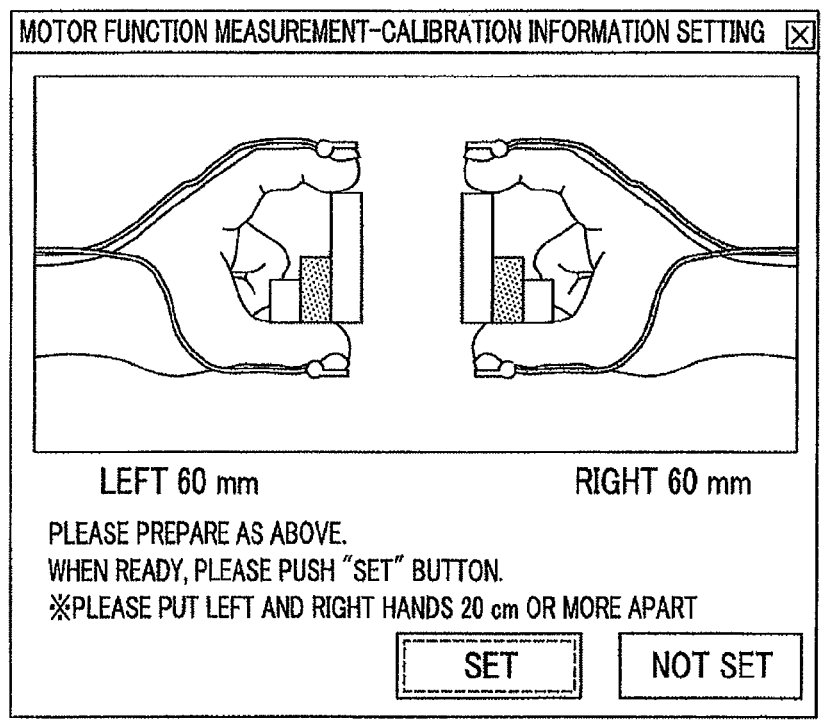
FIG. 20B is a diagram showing an illustrative screen launched when the button for setting the calibration is operated.
Figure 21:
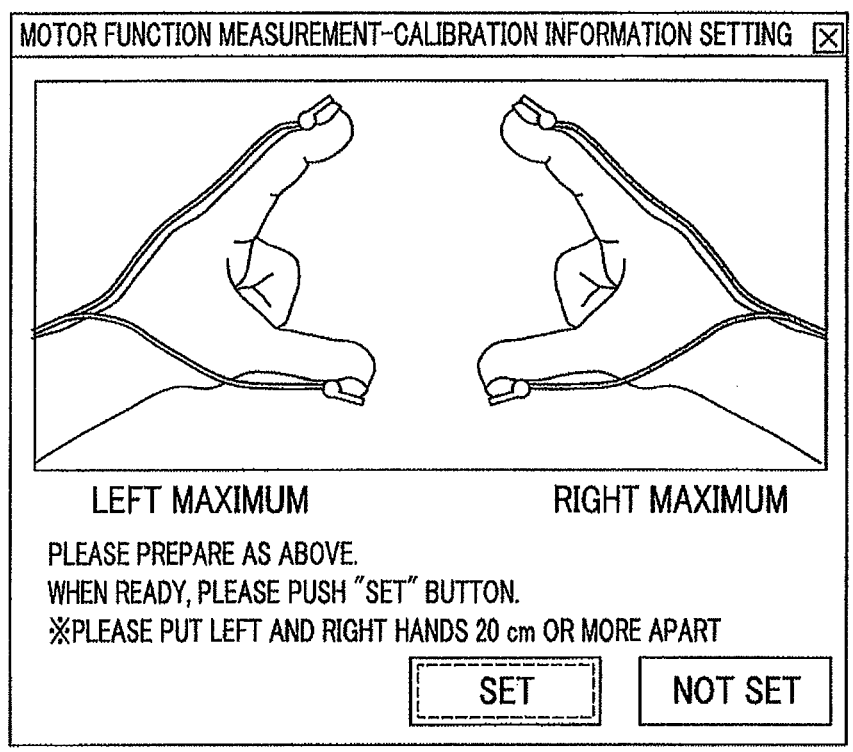
FIG. 21 is a diagram showing an illustrative screen launched when the button for setting the calibration is operated.

FIGS. 20A to 21 show screens launched when the calibration-point measuring unit 3021 (see FIG. 2) is activated. Those screens are launched when the button of calibration setting 3014 (see FIG. 19) is operated, and the screen changes in the order of FIG. 20A, FIG. 20B, and FIG. 21. When the button of calibration setting 3014 is pressed, first, the screen shown in FIG. 20A is displayed, and the subject is caused to slightly close the index finger and the thumb. Next, after the subject holds the 60-mm portion of the calibration block 106 (see FIG. 6, etc.) between the two fingers, when the user operates the button of "set", calibration is executed, and the screen changes to the screen shown in FIG. 20B. Thereafter, when the subject widely opens the two fingers, the calibration is kept executed. After the button of "set" is pressed in the screen shown in FIG. 21, the screen returns to the screen shown in FIG. 19. A distance value between the two fingers when the subject opens the two fingers at a maximum can be calculated from a voltage value obtained through the screen shown in FIG. 21. It is possible to normalize a movement waveform with the size of the hand of the subject using the obtained distance value.

Figure 22:
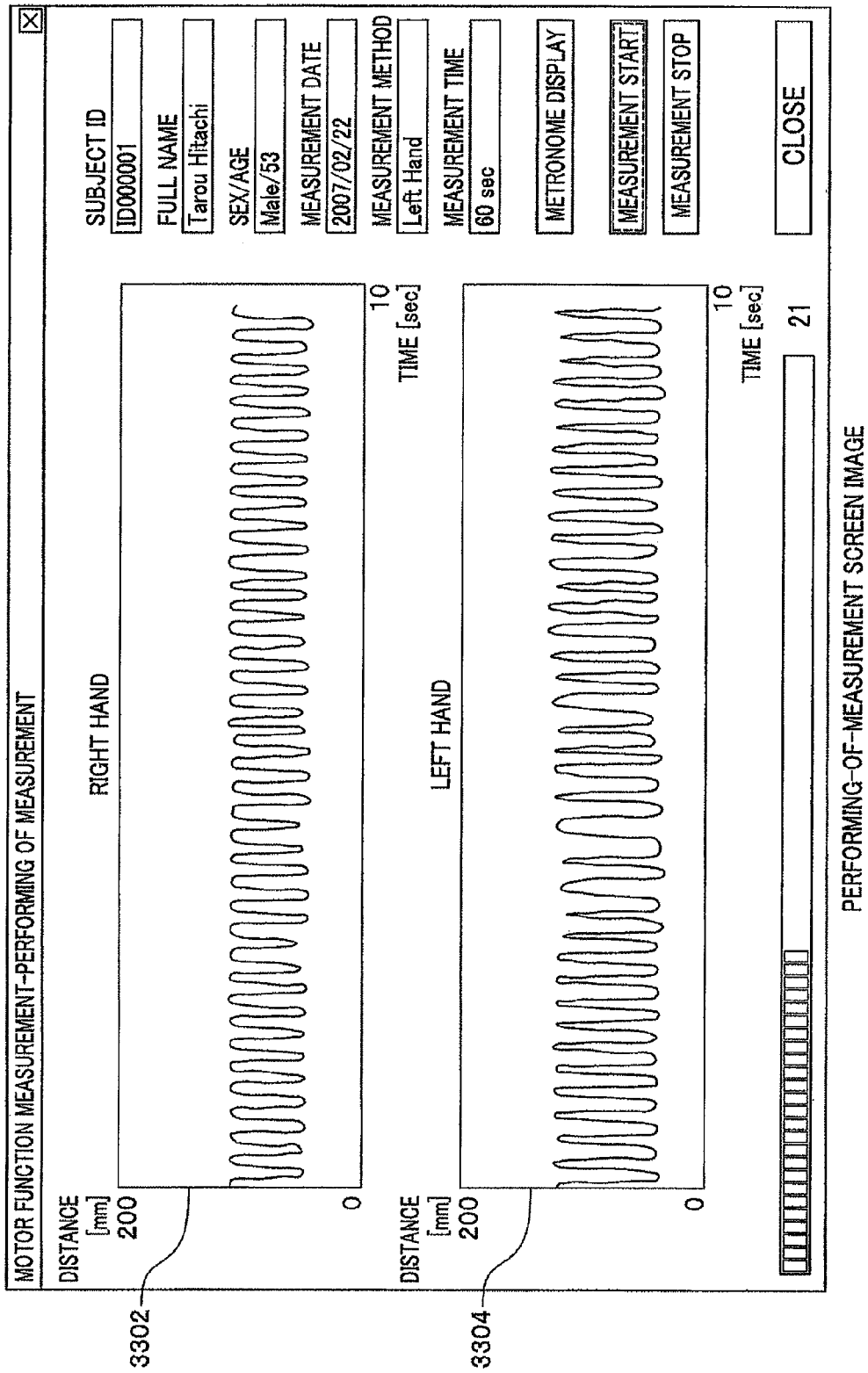
FIG. 22 is a diagram showing an illustrative screen for performing measurement.

FIG. 22 shows an illustrative screen for executing measurement. This screen for executing measurement is launched when the button of "execute measurement 3016" (see FIG. 19) in the measurement setting screen 3000 is operated.

As shown in FIG. 22, the screen for executing measurement displays graphs for the right hand and the left hand, respectively (where the horizontal axis indicates a second and the vertical axis indicates a distance between the cushions of the two fingers). Also, measurement is started (obtaining of data to be analyzed is started) upon operation of the button of "start measurement", and the measurement is terminated (obtaining of data to be analyzed is terminated) upon operation of the button of "terminate measurement". Also, information (e.g., the subject ID) on the subject to be measured is displayed on the upper right of the screen. What is indicated by the graph is a movement waveform obtained by the movement-waveform generating unit 302 shown in FIG. 2 that converts time-series data of a voltage value obtained from the motor function measuring apparatus 12.

The screen for executing measurement also includes buttons of "display metronome" and "close" (to close this screen), and a measurement time display bar (displays a measurement time in a progress bar form) which is located at the lowermost location. A message for confirming saving of measurement information may be displayed when measurement is executed.

Figure 23:
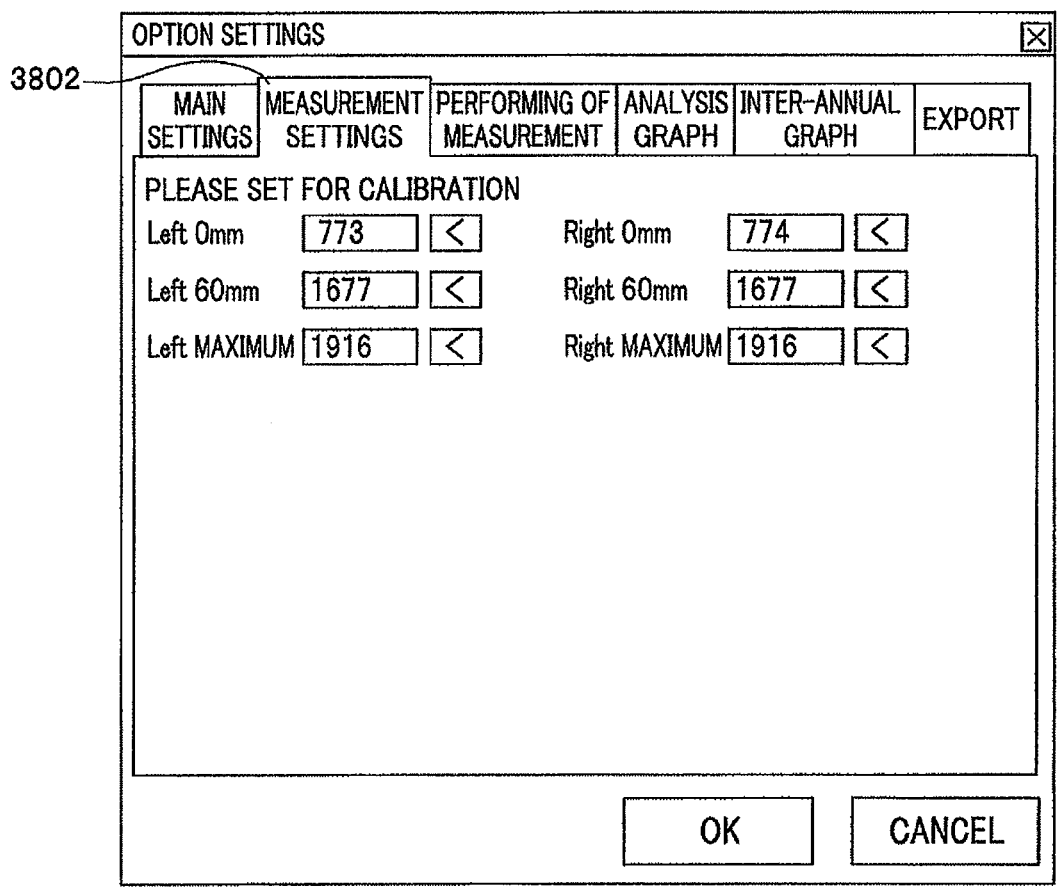
FIG. 23 is a diagram showing an illustrative screen for option setting.

FIG. 23 shows an illustrative option screen (a screen for setting options). The option screen is launched upon operation of the button of "option" in the measurement-data-list screen 2700 (see FIG. 16).

As shown in FIG. 23, when the tab of measurement setting 3802 is selected through the option screen, setting of initial values for a calibration is enabled. Regarding respective values, for example, only numerals can be input, and an operational error is caused when it is NULL.

The voltage value V2 measured by the calibration-point measuring unit 3021 shown in FIG. 2 may be recorded through the option screen shown in FIG. 23. The voltage value V2 is a voltage value measured when the generator coil of the motion sensor 22 and the detector coil thereof maintain a sufficient distance therebetween. The voltage value V2 is recorded as an offset voltage, and is used by the conversion-formula generating unit 3022. The recording is made for each of the right hand and the left hand, and once measured before the apparatus is used, the same value can be used thereafter.

Figure 24:
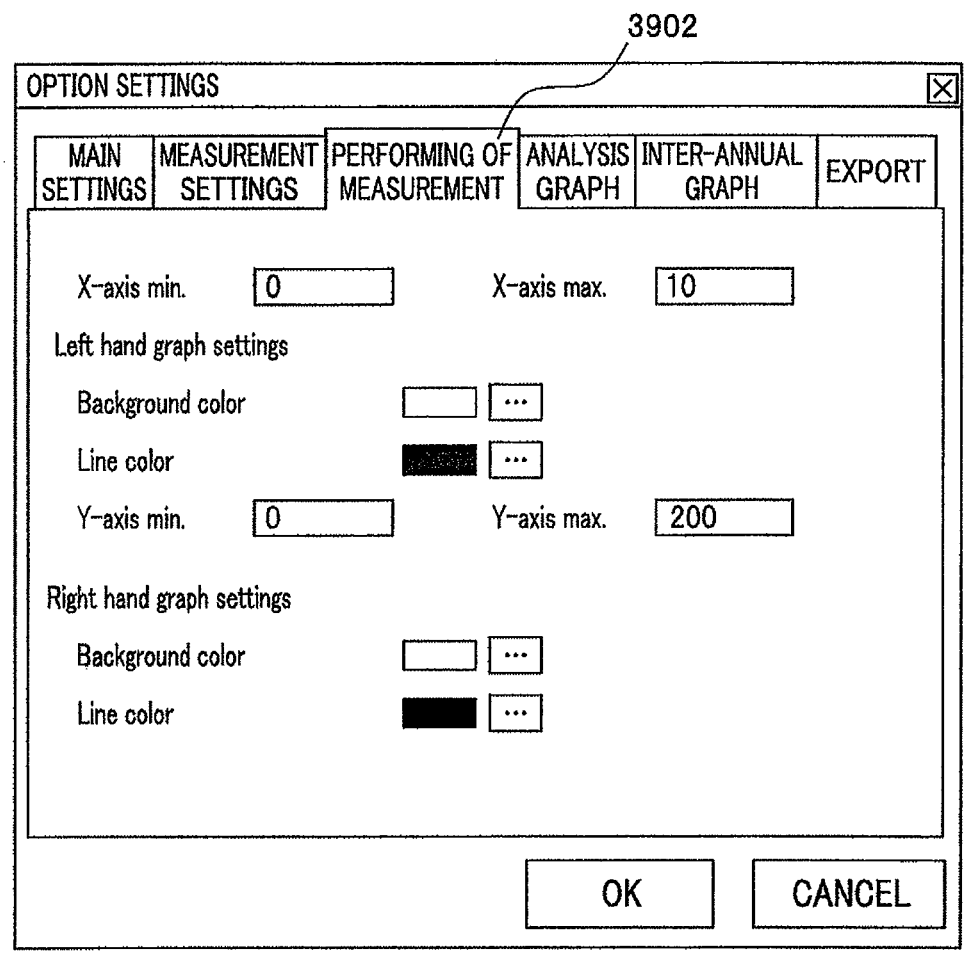
FIG. 24 is a diagram showing another illustrative screen for option setting.

FIG. 24 shows another illustrative option screen (a screen for setting options). As shown in FIG. 24, when the tab of execute measurement 3902 is selected through the option screen, setting of values of various items relating to the screen (see FIG. 22) for executing measurement is enabled. The background color is set to be, for example, white for both right and left hands when no setting is made. The line colors are blue and red for the left hand and the right hand, respectively, when no setting is made. Also, regarding an X-axis minimum value, an X-axis maximum value, a Y-axis minimum value, and a Y-axis maximum value, only numerals can be inputtable.

By using the above-explained screens shown in FIGS. 16 to 24, the motor function measuring system 10 of this embodiment can be realized.

Second Embodiment

Next, a detailed explanation will be given of a second embodiment with reference to the accompanying drawings as needed. The structural elements shown in FIGS. 1 to 12 and screens shown in FIGS. 16 to 24 are same as those of the first embodiment, so that duplicated explanation thereof will be omitted. An explanation will be given of different methods from those of the first embodiment regarding the conversion-formula generating unit 3022 and the movement-waveform converting unit 3023 shown in FIG. 2.

As explained above, the conversion-formula generating unit 3022 generates a conversion formula that converts voltage data supplied from the motor function measuring apparatus 12 into a movement waveform. In this embodiment, finger tapping motions of plural subjects are measured in practice, and a conversion formula (hereinafter, referred to as an individual conversion formula) unique to each subject is generated. Next, those individual conversion formulae are averaged, and a single conversion formula (hereinafter, referred to as a master curve) is calculated. Explanations will be given of the above-explained two processes.

Figure 25:
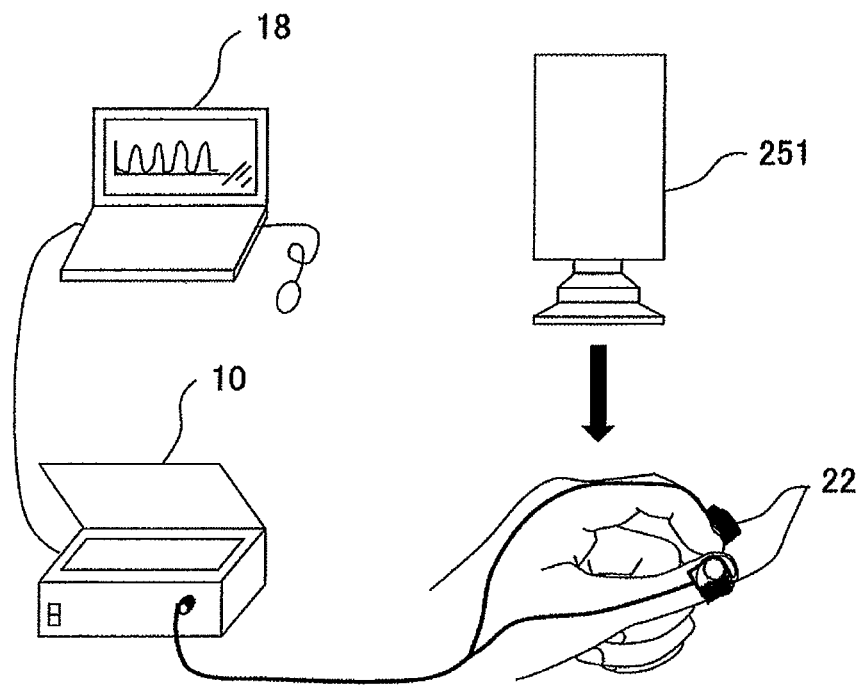
FIG. 25 is a diagram showing a measuring method for creating an individual conversion formula.

In order to generate individual conversion formulae, finger tapping motions of subjects are measured in practice. As shown in FIG. 25, the motion sensors 22 are attached to the fingers of the subject, the subject is caused to perform finger tapping for several periods, and voltage data obtained by the motor function measuring apparatus 12 is recorded. While at the same time of measuring the voltage value, images of the fingers are picked up by a high-speed camera 251, and a distance value between the cushions of the two fingers are extracted from the images. At this time, the lens surface of the high-speed camera is installed so as to be parallel to the plane formed by the index finger and the thumb. In this embodiment, the high-speed camera is used as an instrument that measures a distance value, but the other measuring instruments like a motion capture system can be used.

Figure 26:
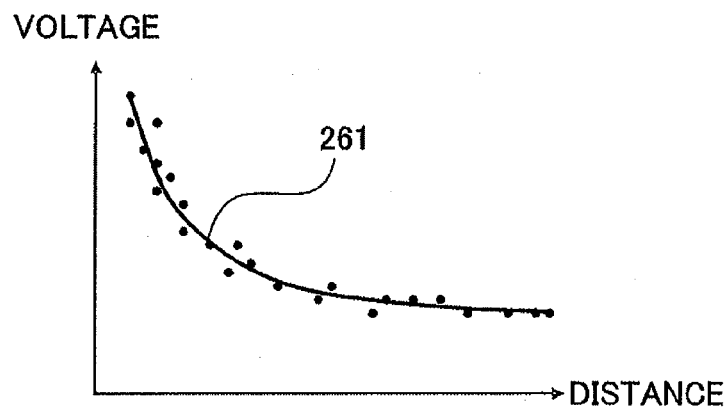
FIG. 26 is a graph showing a relationship between a voltage and a distance used for calculating an individual conversion formula.

Voltage data and distance data obtained thus way are plotted on a scatter diagram as shown in FIG. 26. The horizontal axis represents a distance value between the cushions of the two fingers, and the vertical axis represents a voltage value. Data on the scatter diagram is approximated by a six degree polynomial equation in order to obtain an individual conversion formula fk 261 (where k is an subject number and k=1 to n). As shown in FIG. 26, the individual conversion formula fk 261 has a limited range between the voltage and the distance, so that compensation is necessary at a portion where the distance is small and a portion where the distance is large as will be discussed later. Data on the scatter diagram is approximated by a six degree polynomial equation in this embodiment, but other high-dimensional equations and conversion table can be used as long as data on the scatter diagram can be sufficiently represented.

Figure 27A:
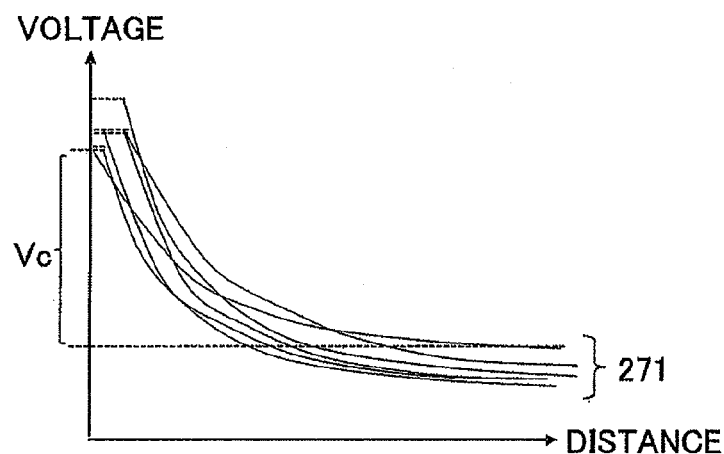
FIG. 27A is a diagram for explaining a master curve.

Next, in order to generate a master curve, n number of individual conversion formulae are generated (where k=1 to n) with plural subjects (the number thereof is n) being as test targets. The n number of individual conversion formulae are taken as a conversion formula group F 271. As shown in FIG. 27A, the range where the voltage values of all conversion formulae in the conversion formula group F 271 overlap is extracted and the extracted range is taken as Vc.

Figure 27B:
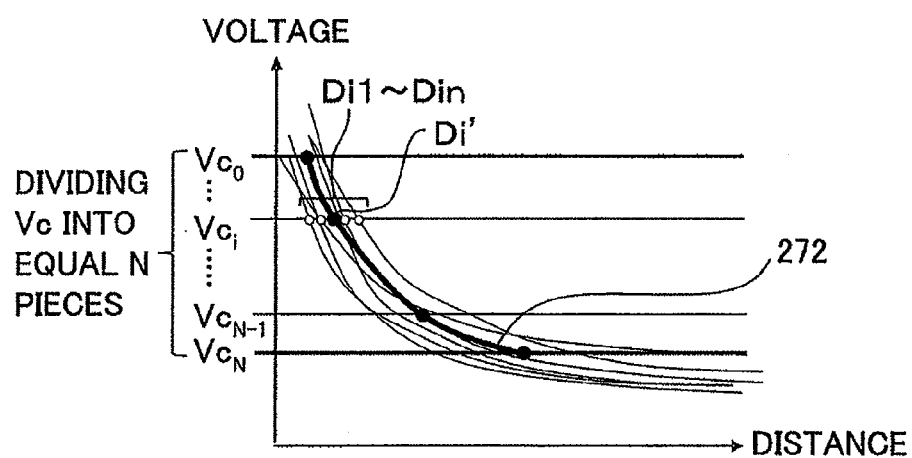
FIG. 27B is a diagram for explaining a master curve.

Next, as shown in FIG. 27B, a voltage value obtained by dividing the extracted range into equal N pieces (where N is a sufficiently large number) is set to be as a voltage value Vci (where i=0 to N). Finally, an individual conversion formula fk is obtained, a distance value Dik (where k is the subject number and k=1 to n) obtained by converting the voltage value Vci is obtained, and an average value of the distance values from Di1 to Din is taken as Di'. [Di', Vci] (where i=0 to N) obtained in this fashion is referred to as a master curve 272.

Figure 28:
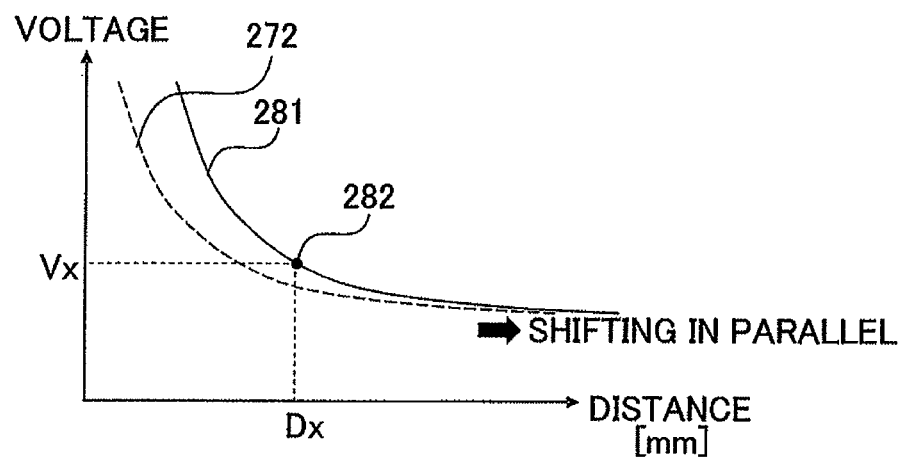
FIG. 28 is a diagram for explaining a method of correcting the master curve shown in FIG. 27B.

The master curve is calculated through an averaging in the distance direction in this embodiment, but may be calculated through an averaging in the voltage direction. Also, without using the obtained master curve as it is, the master curve may be corrected with a calibration point (8) 282 (Dx, Vx) (see FIG. 28) measured using the calibration block 106. More specifically, as shown in FIG. 28, the master curve 272 may be shifted in a parallel manner in the distance direction (or the voltage direction) so as to pass through the calibration point (8) 282, and the shifted master curve is taken as a corrected master curve 281.

Figure 29:
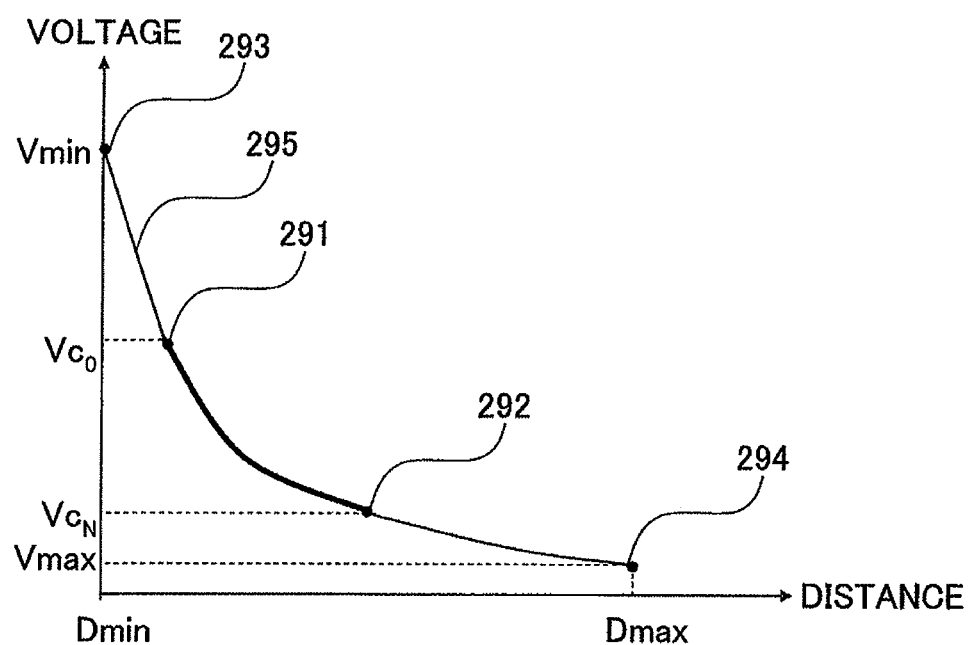
FIG. 29 is a diagram for explaining a method of correcting the master curve shown in FIG. 27B.

As explained above, the master curve is limited within the range of Vc, so that it is necessary to generate a conversion curve through another method for ranges other than the range of Vc. As shown in FIG. 29, regarding portions where the voltage is equal to or higher than Vc0, such portions between a left end 291 of the master curve and a calibration point (6) 293 (Dmin, Vmin) are compensated by a linear polynomial equation. The calibration point (6) 293 stands for a distance and a voltage obtained when the two fingers slightly contact with each other, and Dmin=0.

Likewise, regarding portions where the voltage is equal to or smaller than VcN, such portions between a right end 292 of the master curve and a calibration point (7) 294 (Dmax, Vmax) are compensated by quadratic polynomial equation. Vmax at the calibration point (7) is a voltage obtained when the detector coil of the motion sensor 22 and the generator coil thereof are apart from each other at a maximum, and is a value that is recorded in the apparatus beforehand. The distance value Dmax is a preset value, and is 300 mm in this embodiment. In addition, Dmax may not be 300 mm if Dmax is large enough compared to a distance between the cushions of the two fingers when the subject opens the two fingers at a maximum. Also, the value of Dmax may be an actual measured value Dm (see FIG. 12) between the two coils when the two coils of the motion sensor 22 are apart from each other at a maximum. The voltage value Vmax is measured through the option screen shown in FIG. 23 which was explained in the first embodiment. A linear polynomial equation and a quadratic polynomial equation are used for compensation in this embodiment, but other types of equations and conversion tables may be used. The master curve compensated in this fashion is referred to as a compensated master curve 295.

The movement-waveform converting unit 3023 (see FIG. 2) converts time-series data on a voltage value into a time-series data on a distance value using the compensated master curve 295 obtained by the conversion-formula generating unit 3022. When a movement waveform is generated as explained above, it is sufficient if the calibration point (6) 293 is measured once before each measurement, so that in comparison with the conventional scheme which needs to measure calibration points three times, there is an advantage that the load at the time of measurement is little (twice when correction is performed using the calibration point (8) 282 (see FIG. 28)). Moreover, unlike the first embodiment that approximately represents a relationship between a voltage and a distance through a formula set beforehand, a conversion formula is obtained based on a relationship between a voltage value and a distance value of an actually measured finger tapping motion, so that the precision of the conversion formula is high.

Figure 30A:
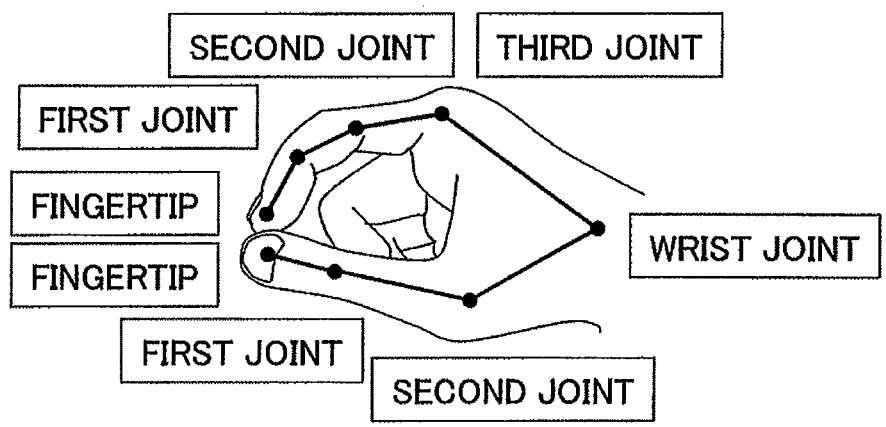
FIG. 30A is a diagram showing how a finger tapping motion is simulated using three-dimensional skeleton model in order to calculate an individual conversion formula.
Figure 30B:
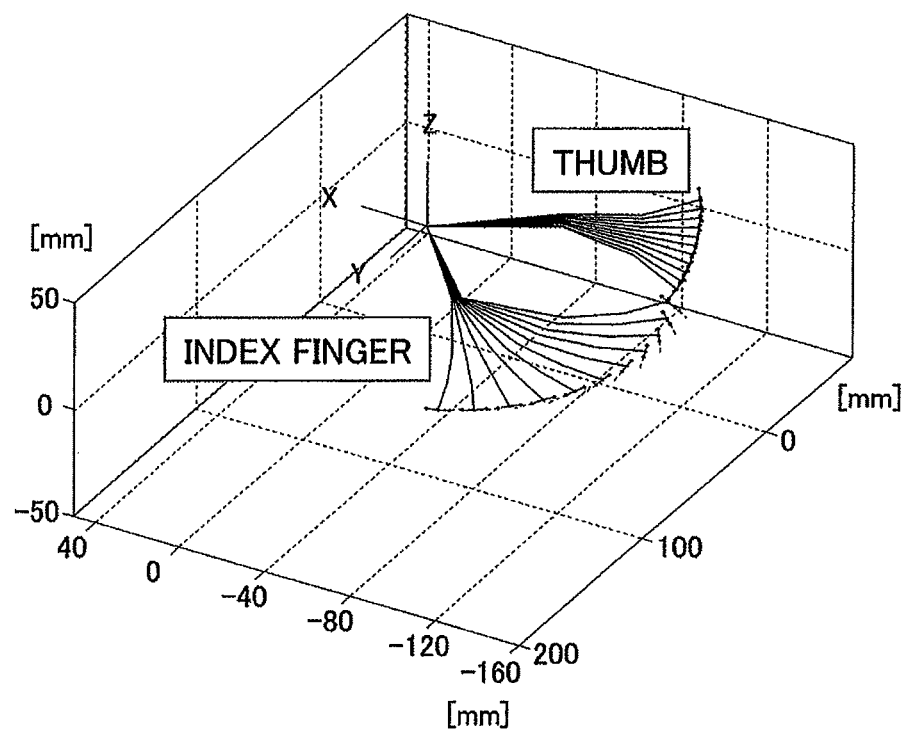
FIG. 30B is a diagram showing how a finger tapping motion is simulated using three-dimensional skeleton model in order to calculate an individual conversion formula.

In order to obtain the individual conversion formula in this embodiment, the finger tapping motion of the subject is actually measured, but the individual conversion formula may be calculated by building a model that simulates the skeleton of the thumb, that of the index finger, and the motions thereof. More specifically, as shown in FIG. 30A, parameters, such as the length of each joint and the angle between joints, are extracted from the image of a finger of the subject, and a three-dimensional skeleton model as shown in FIG. 30B is built using those parameters, and a finger tapping motion is simulated. The three-dimensional model is built based on a presumption that the detector coil and the generator coil are attached to the nail portions of the two fingers. Through this simulation, a distance value between respective cushions of the two fingers is calculated as a linear distance between respective cushions of the two fingers on the three-dimensional skeleton model. The voltage value of the magnetic sensor is obtained by calculating magnetic flux entering in the detector coil from the positional relationship between the generator coil and the detector coil on the three-dimensional skeleton model, and by converting the magnetic flux using the inductance of the apparatus.

The individual conversion formula fk is obtained based on the voltage value and the distance value obtained in this fashion. Likewise, regarding plural subjects, parameters, such as the length of each joint and the angle between the joints, are extracted, and respective finger tapping motions are simulated, thereby obtaining the conversion formula group F. The calculation thereafter is same as the above-explained method. In addition, as the parameters of the skeleton model, an average value of the parameters extracted from the image of the actual finger of the subject or a dispersion value thereof may be used, or a value presumed from literatures may be used, without using the parameters extracted from the image of the actual finger of the subject.

As explained above, according to the motor function measuring apparatus 12 according to the first and second embodiments, it is needless to say that the measurement result by the apparatus can assist not only diagnosis of the severity level of Parkinson's disease but also diagnosis of other movement disorders, such as a neural disease like rheumatism.

Also, through the calibration method explained in the first and second embodiments, a motor function inspection is enabled which is more precise and simpler than the conventional scheme.

That is, according to the above-explained embodiments, a calibration point unique to each apparatus and measured before the apparatus is used and a calibration point unique to each subject and measured every time the subject changes are both used. According to the above-explained embodiments, a voltage value can be converted into a distance value highly precisely by using the calibration point unique to each subject and the number of calibration measurements can be reduced and the measurement is simplified by using the calibration point unique to each apparatus. Accordingly, by using the calibration point unique to each apparatus and the calibration point unique to each subject as needed, a motor function inspection is enabled which is simpler and more precise than the conventional scheme.

As explained above, the conversion-formula generating unit 3022 includes an individual-conversion-formula generating unit, an averaged-conversion-formula generating unit, and a conversion-formula compensating unit.

The individual-conversion-formula generating unit generates a conversion formula based on distance data obtained by causing a predetermined measuring apparatus to measure a distance between predetermined two portions of a biological object to which a magnetic field generator and a magnetic field detector are attached, and magnetic field data detected by the magnetic field detector.

The averaged-conversion-formula generating unit generates an averaged-conversion-formula of plural conversion formulae obtained for plural biological objects by the individual-conversion-formula generating unit.

The conversion-formula compensating unit compensates a range where no distance data is present corresponding to magnetic field data in the averaged-conversion-formula obtained by the averaged-conversion-formula generating unit with an averaged-conversion-formula using a calibration point obtained by the calibration-point measuring unit.

The embodiments of the present invention were explained above, but the present invention is not limited to the above-explained embodiments, and can be changed and modified in various forms within the scope and spirit of the present invention.

For example, when the holder 40 (see FIG. 4) is attached to the finger of the subject, instead of using the adhesive sheet 38, the holder may be attached to the finger by a silicone-made band wrapped therearound.

The above-explained specific configurations can be changed and modified in various forms appropriately without departing from the scope and spirit of the present invention.

What is claimed is:

1. A motor function analyzing apparatus comprising:
a movement-waveform generating unit which includes:
a magnetic field generator that generates a magnetic field, and a magnetic field detector that detects the magnetic field,
where each of the magnetic field generator and the magnetic field detector is respectively attached to one of two predetermined parts of a biological object, and a distance between the two predetermined parts changes with motion of the biological object, and where the movement-waveform generating unit generates a movement waveform based on magnetic field data detected by the magnetic field detector, and the movement-waveform generating unit further includes:

a calibration-point measuring unit that measures calibration points corresponding to the distance between the two predetermined parts of the biological object and the magnetic field data detected by the magnetic field detector;

a conversion-formula generating unit that generates a conversion formula for converting the magnetic field data detected by the magnetic field detector into the movement waveform using the calibration points measured by the calibration-point measuring unit; and a movement-waveform converting unit that converts the magnetic field data detected by the magnetic field detector to generate the movement waveform using the conversion formula generated by the conversion-formula generating unit, wherein the calibration-point measuring unit comprises:

an apparatus-unique-voltage measuring unit that measures an apparatus-unique-voltage of the motor function analyzing apparatus with the magnetic field generator and the magnetic field detector being located apart from each other by a first distance greater than a maximum possible distance between the two predetermined parts of the biological object; and a subject-unique-voltage measuring unit that measures a subject-unique-voltage for the biological object with the magnetic field generator and the magnetic field detector respectively attached to the two predetermined parts of the biological object and located apart from each other by a second predetermined distance, wherein the conversion-formula generating unit generates the conversion formula using a first calibration point corresponding to the apparatus-unique-voltage and a second calibration point corresponding to the subject-unique-voltage.

2. A motor function analyzing apparatus comprising:

a movement-waveform generating unit which includes:

a magnetic field generator that generates a magnetic field, and a magnetic field detector that detects the magnetic field, where each of the magnetic field generator and the magnetic field detector is respectively attached to one of two predetermined parts of a biological object, and a distance between the two predetermined parts changes with motion of the biological object, and where the movement-waveform generating unit generates a movement waveform based on magnetic field data detected by the magnetic field detector, and the movement-waveform generating unit further includes:

a calibration-point measuring unit that measures a calibration point corresponding to distance data between the two predetermined parts of the biological object and magnetic field data detected by the magnetic field detector;

a conversion-formula generating unit that generates an average conversion formula for converting the magnetic field data detected by the magnetic field detector into a movement waveform using the calibration point measured by the calibration-point measuring unit; and a movement-waveform converting unit that converts the magnetic field data detected by the magnetic field detector to generate a movement waveform using the average conversion formula generated by the conversion-formula generating unit, wherein the conversion-formula generating unit comprises:

an individual-conversion-formula generating unit that generates the conversion formula based on distance data obtained by measuring a distance between the two predetermined parts of the biological object to which the magnetic field generator and the magnetic field detector are attached by a predetermined measuring apparatus, and the magnetic field data detected by the magnetic field detector; and an averaged-conversion-formula generating unit that generates an average conversion formula by calculating an average distance value for each of a plurality of voltage values based on a plurality of conversion formulae obtained for a plurality of biological objects by the individual-conversion-formula generating unit.

3. The motor function analyzing apparatus according to claim 2, wherein the conversion-formula generating unit includes a conversion-formula compensating unit that compensates the average conversion formula for a range where no distance data corresponding to the magnetic field data is present in the average conversion formula generated by the averaged-conversion-formula generating unit using the calibration point obtained by the calibration point measuring unit.

4. The motor function analyzing apparatus according to claim 2, wherein the individual-conversion-formula generating unit measures the distance data between the two predetermined parts of the biological object to which the magnetic field generator and the magnetic field detector are attached, and the magnetic field data.

5. The motor function analyzing apparatus according to claim 2, wherein the individual-conversion-formula generating unit calculates the distance data and the magnetic field data by modeling a motion of the two predetermined parts of the biological object on a computer.

6. The motor function analyzing apparatus according to claim 1, wherein the apparatus-unique-voltage measuring unit measures the apparatus-unique-voltage in a state that no magnetic field is detected by the magnetic field detector.

7. The motor function analyzing apparatus according to claim 1, wherein the apparatus-unique-voltage measuring unit measures the apparatus-unique-voltage in a state that the magnetic field detector and the magnetic field generator are located a maximum distance from each other.

8. The motor function analyzing apparatus according to claim 1, wherein the subject-unique-voltage measuring unit measures the subject-unique-voltage in a state that the second predetermined distance is approximately 0.

* * * * *